United States Patent
Colthurst

(10) Patent No.: US 8,014,876 B2
(45) Date of Patent: Sep. 6, 2011

(54) TREATMENT APPARATUS FOR APPLYING ELECTRICAL IMPULSES TO THE BODY OF A PATIENT

(75) Inventor: James Colthurst, Hungerford (GB)

(73) Assignee: Fenzian Limited (GB)

(*) Notice: Subject to any disclaimer, the term of this patent is extended or adjusted under 35 U.S.C. 154(b) by 186 days.

(21) Appl. No.: 12/180,019

(22) Filed: Jul. 25, 2008

(65) Prior Publication Data
US 2008/0281382 A1    Nov. 13, 2008

Related U.S. Application Data

(62) Division of application No. 10/563,996, filed as application No. PCT/GB2004/004552 on Oct. 28, 2004, now Pat. No. 7,483,734.

(30) Foreign Application Priority Data

May 28, 2004 (GB) .................................. 0412070.5

(51) Int. Cl.
*A61N 1/18* (2006.01)
(52) U.S. Cl. ....................................... 607/145; 128/907
(58) Field of Classification Search .................. 128/907; 607/2, 145
See application file for complete search history.

(56) References Cited

U.S. PATENT DOCUMENTS

| | | | |
|---|---|---|---|
| 4,112,923 A | 9/1978 | Tomecek | |
| 4,541,432 A | 9/1985 | Molina-Negro et al. | |
| 4,630,615 A | 12/1986 | Yomtov | |
| 4,646,744 A | 3/1987 | Capel et al. | |
| 4,694,840 A | 9/1987 | Kairis et al. | |
| 4,917,093 A | 4/1990 | Dufresne et al. | |
| 4,944,302 A | 7/1990 | Hernandez et al. | |
| 5,251,637 A | 10/1993 | Shalvi | |
| 5,339,827 A * | 8/1994 | Masopust | 600/548 |
| 5,385,150 A | 1/1995 | Ishikawa | |
| 5,426,387 A | 6/1995 | Teillaud et al. | |
| 6,301,500 B1 | 10/2001 | Van Herk et al. | |
| 6,421,560 B1 * | 7/2002 | Yoo | 600/548 |

(Continued)

FOREIGN PATENT DOCUMENTS

CN    1448109 A    10/2003

(Continued)

OTHER PUBLICATIONS

Kosmed Course Manual Basic—Part 1; Issue: B1M Oct. 2001.

(Continued)

*Primary Examiner* — Scott M Getzow
*Assistant Examiner* — Amanda Patton
(74) *Attorney, Agent, or Firm* — Andrus, Sceales, Starke & Sawall, LLP

(57) ABSTRACT

The present invention provides a treatment device for applying electrical impulses to a living body through the skin, for treating a variety of clinical conditions. The device comprises a pair of electrodes for contact with the skin, and a waveform generator for repeatedly generating an AC waveform for applying electrical impulses through the electrodes to the skin. A detector detects changes in the skin impedance and generates detector output signals representing the skin impedance. Means responsive to the detector output signals for monitor the responsivity of the skin, and indicator means activated by the monitoring means generate a first indication when a predetermined level of responsivity is reached and a second indication when a pre-determined treatment has been administered.

9 Claims, 18 Drawing Sheets

U.S. PATENT DOCUMENTS

| | | |
|---|---|---|
| 6,584,358 B2 | 6/2003 | Carter et al. |
| 6,662,051 B1 | 12/2003 | Eraker et al. |
| 6,760,627 B2 | 7/2004 | Carter et al. |
| 6,792,315 B2 | 9/2004 | Carter et al. |
| 6,853,863 B2 | 2/2005 | Carter et al. |
| 2001/0032098 A1 | 10/2001 | Kulkarni |
| 2002/0026225 A1 | 2/2002 | Segal |
| 2002/0095080 A1 | 7/2002 | Cory et al. |
| 2003/0163068 A1 | 8/2003 | Kang |
| 2003/0208248 A1 | 11/2003 | Carter et al. |
| 2004/0082979 A1 | 4/2004 | Tong et al. |
| 2004/0087838 A1* | 5/2004 | Galloway et al. ............ 600/300 |
| 2004/0204962 A1 | 10/2004 | Howser et al. |
| 2005/0033381 A1 | 2/2005 | Carter et al. |
| 2005/0043775 A1 | 2/2005 | John et al. |
| 2005/0187591 A1 | 8/2005 | Carter et al. |

FOREIGN PATENT DOCUMENTS

| | | |
|---|---|---|
| EP | 0 145 176 A2 | 6/1985 |
| EP | 0 145 176 B1 | 6/1985 |
| EP | 1 246 665 B1 | 8/2005 |
| FR | 2 418 646 A1 | 9/1979 |
| SU | 1560230 A1 | 4/1990 |
| SU | 1817335 A1 | 8/1995 |
| TW | 254857 | 8/1995 |
| TW | 495355 B | 7/2002 |
| TW | 515276 Y | 12/2002 |
| TW | 555578 B | 10/2003 |
| WO | 03/086535 A | 10/2003 |

OTHER PUBLICATIONS

Kosmed Course Manual Basic—Part 2; Issue: B2M Jul. 2001.
International Search Report for corresponding application PCT/GB2004/004552 mailed Jul. 12, 2005.
European Patent Office Search Report for Great Britain Patent Application No. GB0412070.5 dated Sep. 16, 2004.
"Mapping Acupuncture Points Using Multi Channel Device", Australasian Physical and Engineering Sciences in Medicine, Australasian College of Physical Scientists in AU, vol. 21, No. 2, 1998, pp. 68-72, G. Kwok, M. Cohen & I. Cosic (XP-000911092).
Taiwanese Search Report for corresponding application TW 094115575, having a completion date of Sep. 17, 2009.

* cited by examiner

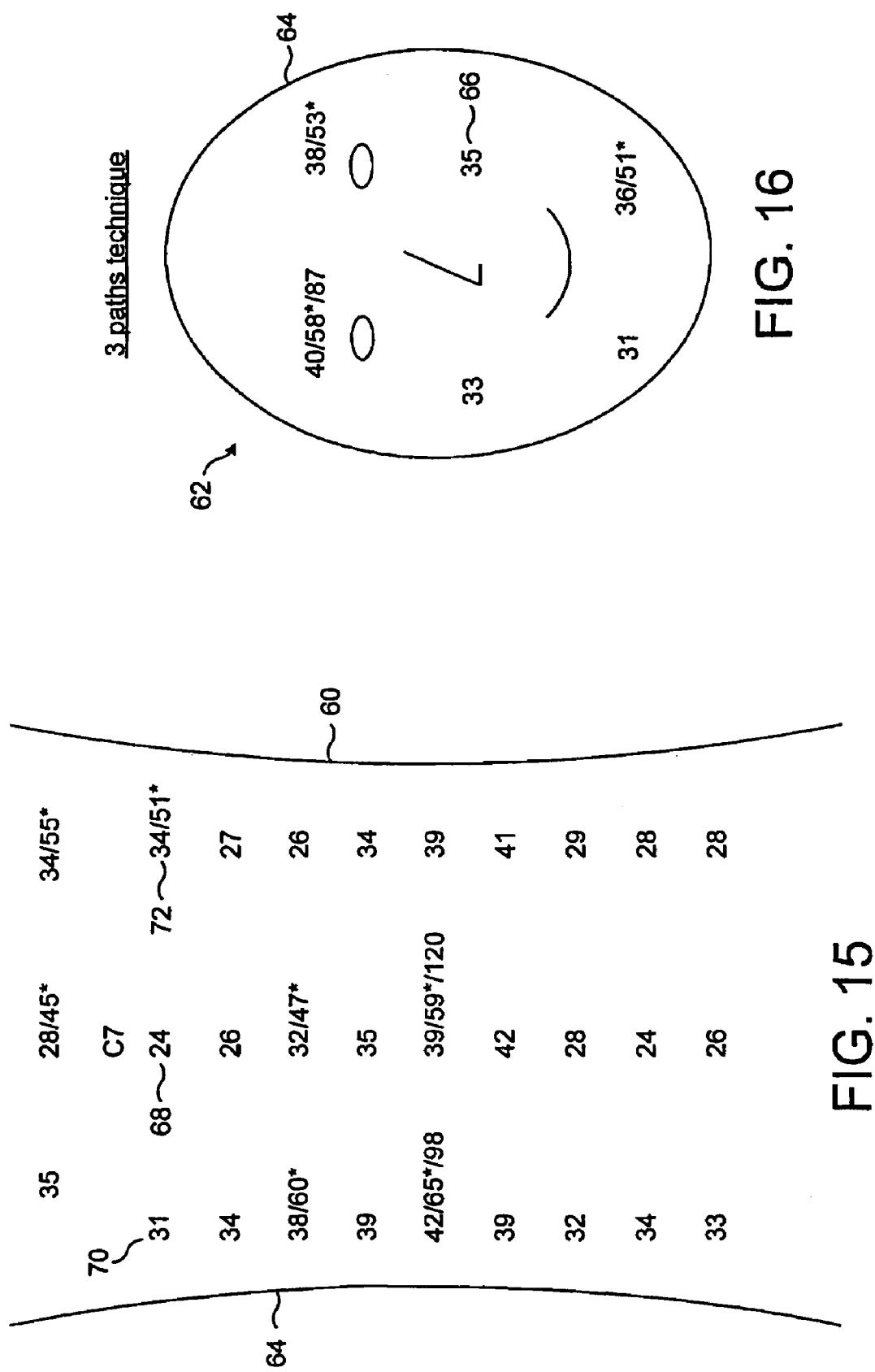

TREATMENT APPARATUS FOR APPLYING ELECTRICAL IMPULSES TO THE BODY OF A PATIENT

CROSS-REFERENCE TO RELATED APPLICATIONS

The present application is a divisional of co-pending U.S. patent application Ser. No. 10/563,996, filed Jan. 19, 2007, which application is incorporated herein by reference and which is the U.S. national stage application of International Application No. PCT/GB2004/004552, filed Oct. 28, 2004, which application is incorporated herein by reference. The International application claims priority of British Patent Application 0412070.5, filed May 28, 2004, which application is incorporated herein by reference.

This invention relates to treatment apparatus for applying electrical impulses to a living body through the skin for treating a variety of clinical conditions.

In particular, in its preferred form at least, the invention relates to a handheld treatment device, and to a treatment apparatus and treatment system including such a device, in which the device makes physical contact with the skin and a repeatedly generated AC waveform is supplied to the electrodes for application at the surface of the skin and for monitoring changes in the skin impedance.

It is known to treat animals and humans by the use of electromagnetic radiation. However, such treatment apparatus is generally cumbersome and expensive to manufacture and run, and usually only has application in certain specific clinical conditions. Furthermore, treatment is often costly and success rates may be low.

It is also known to employ handheld scanning devices using electromagnetic radiation for assistance in the development of treatments for animals and humans. However, these devices again tend to be limited in their application.

There is therefore a need for more inexpensive, portable equipment that is both flexible and easy to use and that is capable of treating a wide variety of clinical conditions.

The present invention seeks to provide a new treatment device, which is effective and easy to use and which has a wide range of clinical applications.

In its preferred form at least, the invention also seeks to provide a handheld device for the treatment of a wide variety of clinical indications.

Another aim of the present invention is to provide a treatment method, device and apparatus, which are non-invasive and which demonstrate benefits in the treatment of a variety of clinical conditions with few harmful side effects.

In brief, the present invention concerns a treatment device, apparatus, system and method for applying electrical impulses of relatively high amplitude and short duration to the body of an animal or patient through the skin for stimulating repair processes within the body.

The invention, at least in its preferred form described below, depends on using alternating current electrostimulation via a biofeedback system based on reaction to skin impedance. The impulses from the device are preferably of short duration (10 μs approx) and of relatively high amplitude (80v). The influence is critically controlled by careful observation using specific measured parameters of the impulses depicted on the device screen. Due to the short duration of impulse the energy of the signal is extremely small and harmful effects highly unlikely.

The equipment is able to detect the zones of lowest skin impedance in an 'area of possibility' (between two concentric rectangular electrodes) and to denote these by numerical readout. Dialogue is initiated through the low resistance points of the skin and guided by observation of this dialogue by a trained practitioner.

Via nerve endings the afferent impulses from the device enter the central nervous system (CNS) at the anterior horns of the spinal cord. Both myelinated and unmyelinated nerves are stimulated by the impulses. By numerical supremacy the majority of the dialogue takes place via the c-fibres. Impulses are conducted up the dorsal and ventral spinothalamic tracts, the dorsal and ventral spino cerebellar tracts and the spino tectal tracts. There is a contribution via the reticulo-cerebellar fibres and the pontine tegmentum. Some of the facilitatory effects of the electrostimulatory system are believed to be mediated by this part of the reticular formation. Continuation of the reticular formation communications beyond the brain stem to the cortex with associated influence on cortical responses is also anticipated. Efferent signals descend via the corticospinal tracts. Frequently, more than one segmental levels are influenced simultaneously.

Electrostimulatory influences have small local effects in the form of polarisation of molecules and local vasomotor effects; with some possible influence on the graded potentials locally. Mediation of local influences is via neuropeptide release.

The majority of the beneficial influence is via efferent nerves from the CNS. At a segmental level, there is also sometimes influence on pain pathways via the saturation of transmitter at the site of entry into the lateral spinothalamic tract, particularly if there is marked A fibre involvement.

Electrostimulation signals act on both local reflex arcs (also influencing the sympathetic chain) with their concomitant effects on internal organ, vessels and muscles; as well as entering the CNS via the ascending tracts for higher connections which will lead to general neuropeptide release (with resultant effect on general homoeostasis), endocrine release, parasympathetic influence and efferent signals down the corticospinal tracts to the relevant levels. Processes of disease control and pain with this form of electrostimulation are mainly mediated via the descending impulses in the CNS to an appropriate level for subsequent peripheral 'local' neuropeptide release. Further mediation is influenced through the autonomic nervous system both via local effects and general physiology.

According to a first aspect of the present invention there is provided a handheld treatment device for applying electrical impulses to a living body through the skin, for treating a variety of clinical conditions, comprising: a pair of electrodes for contact with the skin; a waveform generator for repeatedly generating an AC waveform for applying electrical impulses through the electrodes to the skin; a detector for detecting changes in the skin impedance and for generating output signals representing the skin impedance; means responsive to the output signals from the detector for monitoring the responsivity of the skin; and indicator means for generating a first indication when a predetermined level of responsivity is reached and a second indication when a pre-determined treatment has been administered.

In a preferred embodiment, the skin impedance alterations, which occur as a result of both the local and general state, are depicted numerically on a screen of the treatment device and influence the next outgoing signal from the device. Moreover, several other aspects of the signal exchange between the skin and the treatment device may be depicted numerically on the screen (amplitude, rate, gradient, speed and so on). Some of these numbers use mathematical algorithms to be able to generate the best possible use of the electrostimulatory dialogue. The numerical representations may then be used by the practitioner to guide the treatment processes, via a number of protocols. The intention is to guide the locked or disturbed CNS foci into a restorative state, thereby initiating or re-stimulating normal repair processes, both centrally and locally. Due to the strong CNS (vs. local) component of the process of exchange, 'old' foci from previous pathological states can be influenced simultaneously, leading also to unexpected resolutions of past disease states.

In its preferred form, the treatment device is a handheld battery powered device.

Advantageously, the detection means generates output signals in the form of pulses whose duration represents the skin impedance; the monitoring means measures the duration t of each pulse; and the indicating means is arranged to generate each indication when t satisfies a predetermined function of t.

Preferably, the indicating means is arranged to generate the first indication when $t_2=4.087\, t_1^{0.7131}$ and to generate the second indication when $dZ/dt=0$.

Conveniently, the electrical impulses generated by the handheld device are of high initial amplitude and brief duration. The resulting treatment is non-invasive and is believed to generate few harmful side effects. The device has been found during trial to be extremely effective in treating a wide variety of clinical indications.

The handheld device according to the invention has a number of advantages, including its ease of use and versatility, as well as the fact that the treatment cost is low while the success rate promises to be relatively high.

According to another aspect of the present invention, there is provided treatment apparatus for applying electrical impulses to a living body through the skin, for treating a variety of clinical conditions, comprising: a pair of electrodes for contact with the skin; a waveform generator for repeatedly generating an AC waveform for applying electrical impulses through the electrodes to the skin; means responsive to a resistance generated between the electrodes due to the skin impedance for detecting the responsivity of different zones of a pre-determined area of the body and for producing output data representing the responsivity of each zone; a store for the output data; and means for selecting a treatment zone from amongst the different zones based on an evaluation of the output data to select the zone of greatest responsivity.

Preferably, the output data from the detecting means is in the form of numerical values, and the selecting means evaluates the output data on the basis of the highest values.

In the preferred embodiment described below, the selecting means comprises means for processing the output data contained in the store, and a display operable by the processing means for indicating the selected treatment zone. For example, the display may be arranged to display a body map of the pre-determined treatment area with the respective output data being displayed at a plurality of map locations representing the corresponding zones of the pre-determined area.

According to a further aspect of the present invention, there is provided a treatment system for the treatment of a living body, comprising: a treatment device for applying electrical impulses to the body through the skin, the treatment device including a CPU; a PC for storing patient records; a cradle for the treatment device, the cradle being connected to or incorporated as a part of the PC; and means for receiving a smart card including a unique patient ID and for providing access to the patient records associated with the unique patient ID.

Advantageously, the smart card may be arranged to carry a PIN number as well as the unique patient ID, and the system may include input means by which a patient may be requested to supply their PIN number. When a match occurs between the input PIN number and the PIN number of all the unique patient ID on the smart card, then the system is arranged to enable access between the treatment device and the practitioner's PC.

A further aspect of the invention features a method of treating or a human or animal through the skin by means of the present treatment device.

According to this aspect of the invention, there is provided a method of treating a living body through the skin, comprising the steps of: placing a pair of electrodes in contact with the skin; generating an AC waveform to supply electrical impulses through the electrodes to the skin; detecting changes in the skin impedance and generating output signals representing the skin impedance; monitoring the responsivity of the skin; and indicating firstly when a predetermined level of responsivity is reached and secondly when a predetermined treatment has been administered.

The invention is described further, by way of example, with reference to the accompanying drawings, in which:

FIGS. 15 and 16 are representations of body treatment maps, which are developed during treatment and displayed on a display of the treatment device;

Referring initially to FIGS. 1 to 5, the present invention comprises a handheld treatment device 10 for applying electrical impulses to a human or animal body through the skin.

Figure 1:
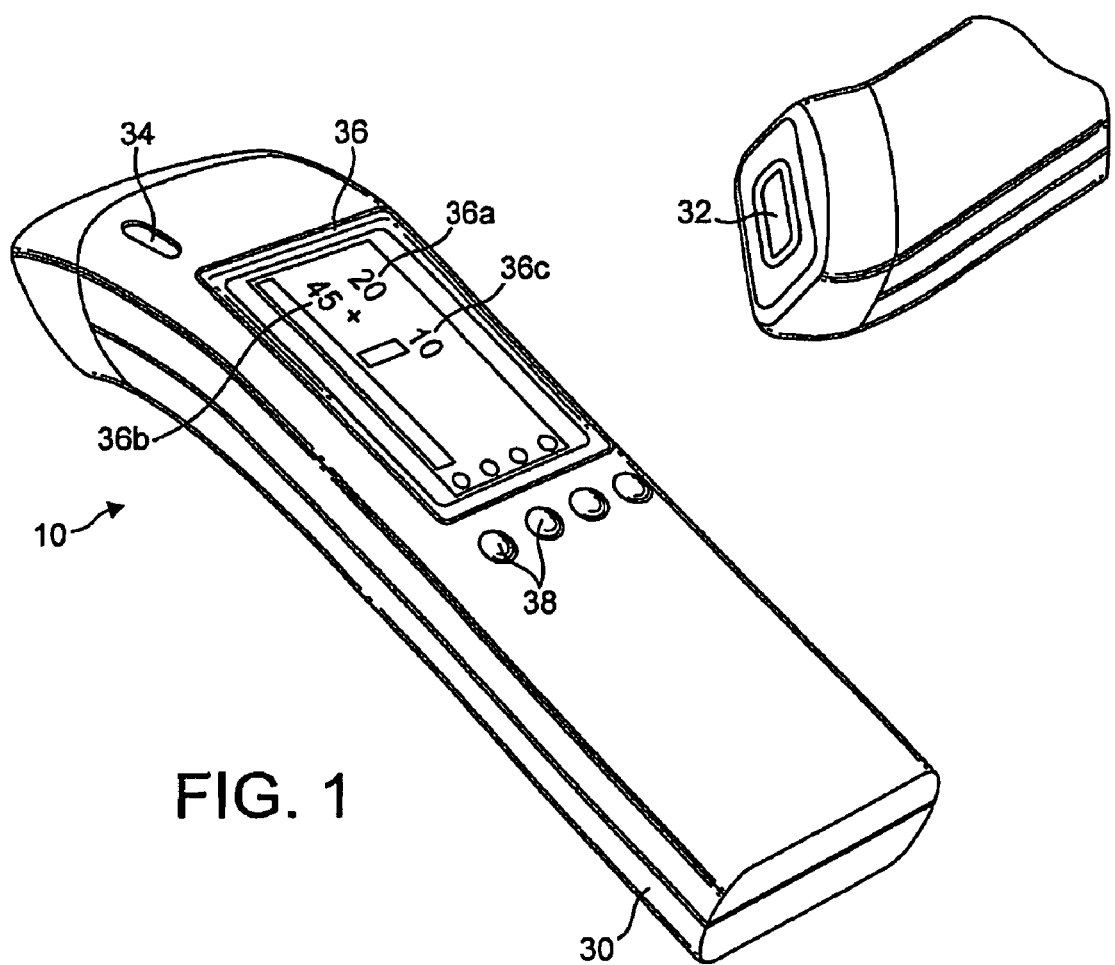
FIG. 1 is a perspective view of a handheld treatment device according to the present invention.

For the purposes of the present description, the treatment of a human being will be described. The treatment device 10 is illustrated in FIG. 1 and is designed to be placed in contact with the skin and to generate short AC electrical impulses for application to the skin by way of electrodes (described below).

Figure 2:
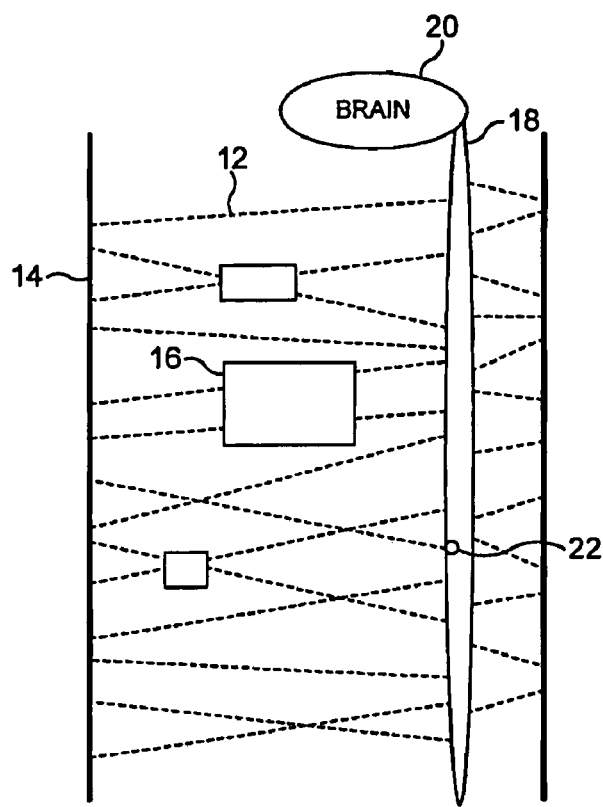
FIG. 2 is a diagram representing the nervous system within the human body.
Figure 3:
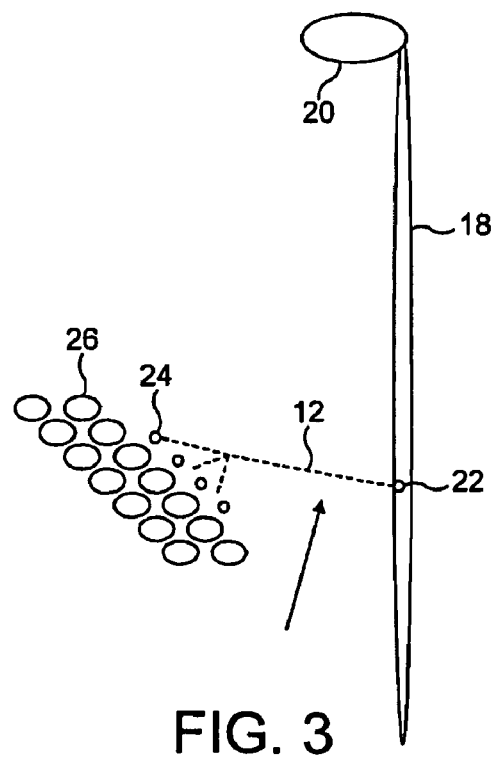
FIG. 3 is a diagram representing the transmission of information from the central nervous system of the body to the cells of body organs.

Referring now to FIG. 2, the body's maintenance system is derived from the embryological layer known as the neuroectoderm. The skin, the nervous system of the body and the spinal cord are all derived from this embryological layer and consequently are all in mutual communication. FIG. 2 shows how a network of nerve fibres 12 connect the skin 14 to various organs 16 of the body and to the spinal cord 18 with its central nervous system and its connection to the brain 20. Information from the control centre 22 of the central nervous system controls the release of specific neuro peptides 24 at the nerve endings, which in turn controls the replacement structure and behaviour of cells 26 within the body organs 16 as indicated in FIG. 3. The network 12 of nerve fibres also controls the transmission of information between the skin 14 and the central nervous system, and abnormalities in the body are reflected via this network 12 in changes in the impedance of the skin 14.

Figure 4:
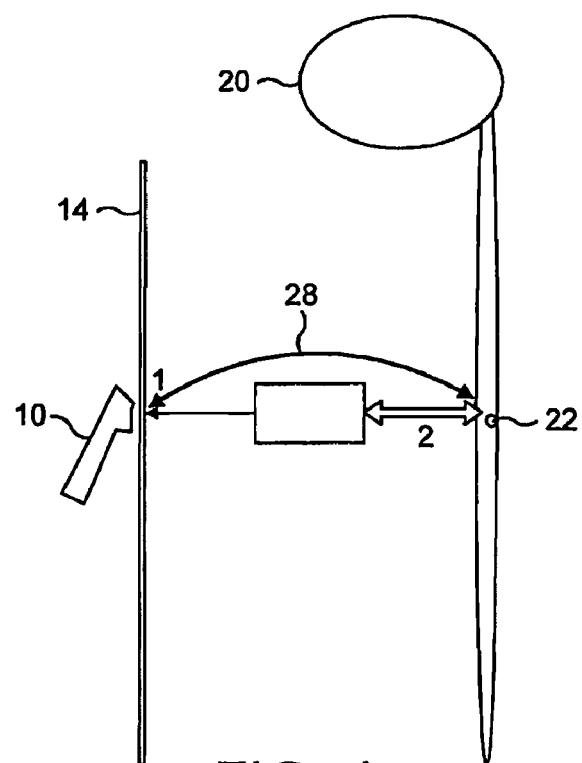
FIG. 4 is a diagram demonstrating use of the treatment device of FIG. 1.
Figure 5:
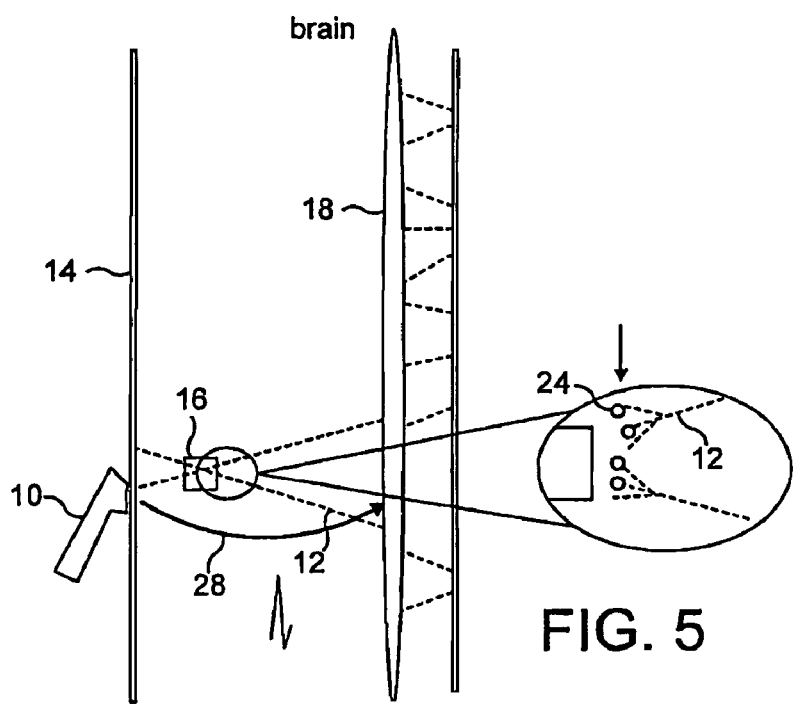
FIG. 5 is an elaboration of FIG. 4.

FIGS. 4 and 5 indicate how the application of the AC electrical impulses from the treatment device 10 at carefully selected locations of the skin 14 may transmit information via a communication pathway 28 through the nerve network 12 to the control centre 22 of the central nervous system and stimulate this control centre into triggering neuro peptide release for activating repair processes in the organs 16. Changes in skin impedance ensue and can be detected by the treatment device 10. Thus, a dialogue between the device 10 and the control centre 22 of the central nervous system, via the skin 14 and the nerve network 12, is initiated and can be employed to trigger repair and to monitor the treatment process and its effects. The treatment is non-invasive and only very small amounts of energy are applied to the body and hence harmful effects are highly unlikely.

Figure 6:
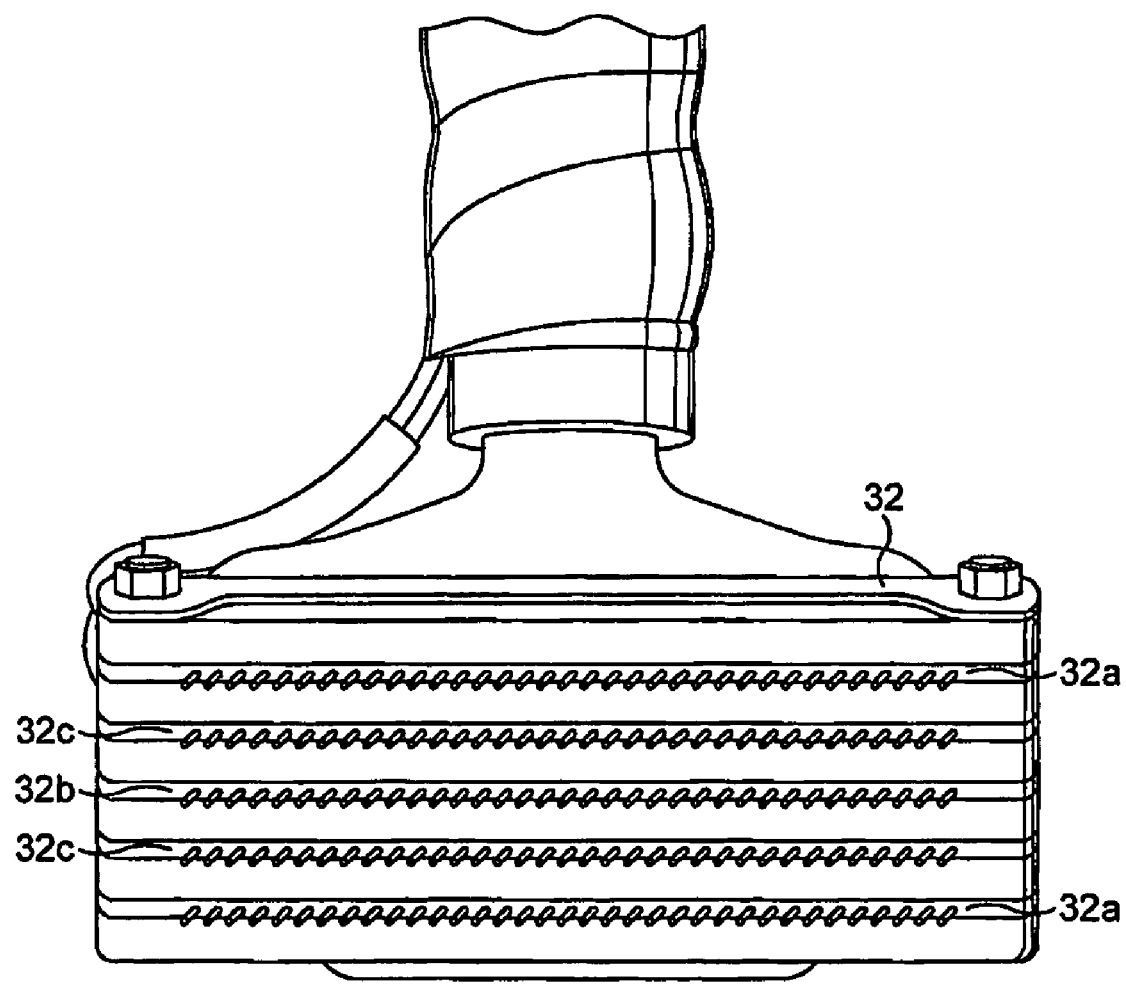
FIG. 6 is a diagram of the electrodes of the treatment device of FIG. 1.

The device itself will now be described further with reference to FIGS. 1, 6 and 7.

The treatment device 10 comprises a body 30 having a pair of electrodes 32 at one end and having on its back an on or off switch 34, a display 36 and a series of user control buttons 38. Four such buttons are shown in FIG. 1, but there may be any number depending on the number of different functions that may be controlled by the user.

The electrodes 32 have a very specific form designed primarily to ensure skin contact whether the skin is bare or is covered by hair or fur. More particularly, the electrodes are designed as a series of five parallel combs, in which the two outermost combs 32a constitute one electrode; the central comb 32b constitutes the other electrode, and the remaining two combs 32c flanking the central comb 32b are insulating elements. The electrodes 32a and 32b are therefore formed from a conductive material, while the combs 32c are formed from an insulating material. The dimensions of the combs are, however, identical, and each comb comprises a series of teeth arranged approximately 2.5 mm apart and having a length of approximately 2 mm.

Figure 7:
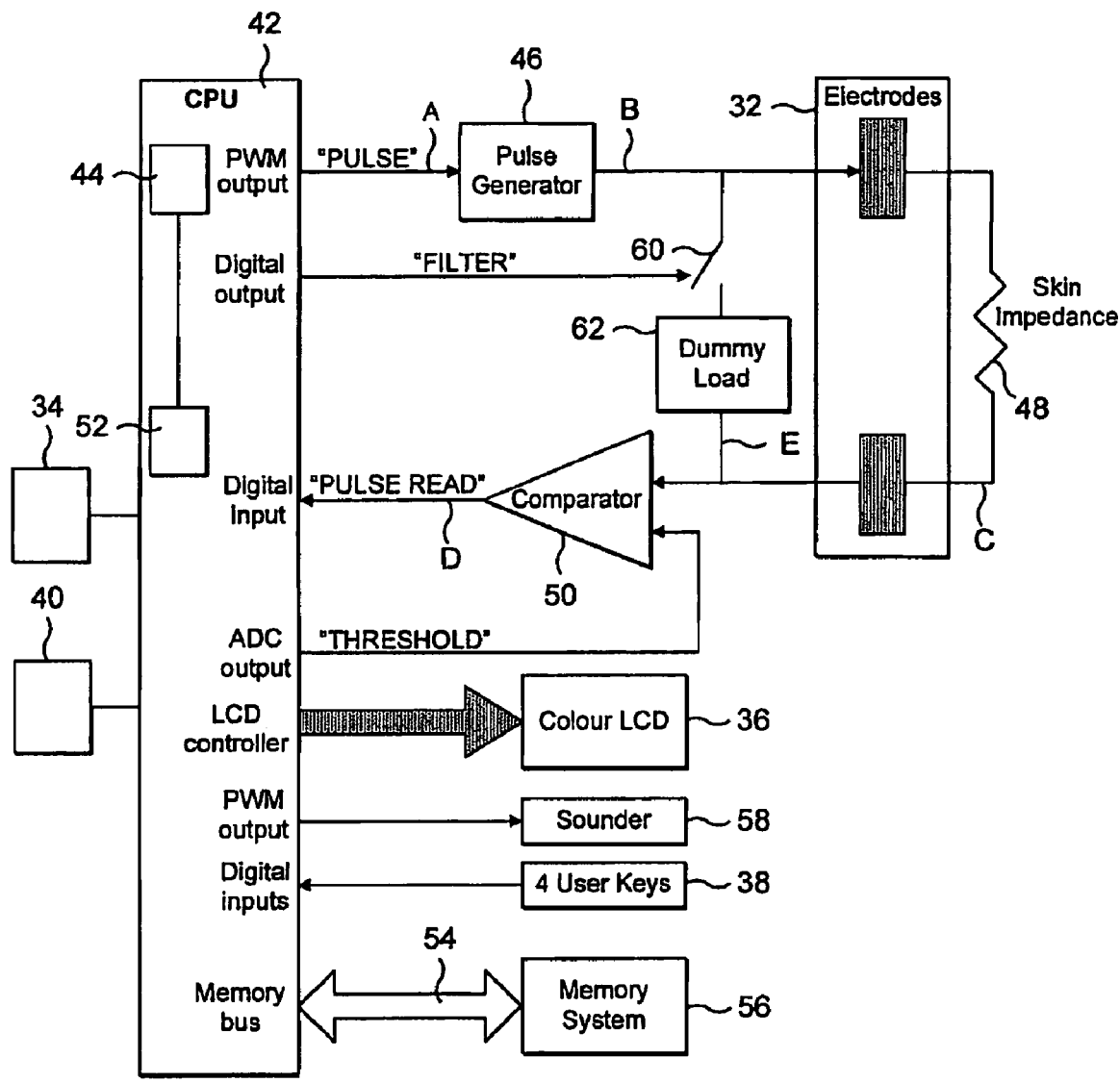
FIG. 7 is a block diagram of the circuitry within the treatment device of FIG. 1.

The electrical circuitry within the treatment device 10 is shown in FIG. 7 and is controlled by the on/off switch 34 and powered by a battery 40 for applying AC electrical impulses to the electrodes 32.

As shown, a central processing unit (CPU) 42 including a clock 44 is arranged to generate an output at point A of FIG. 7 in the form of a train of rectangular pulses. Such pulses are supplied to a waveform generator 46 for triggering an output from the generator at point B of the circuit. The output of the waveform generator 46 is an AC decaying oscillation, which is repeatedly triggered by the pulses from the CPU 42 and which is applied to one of the electrodes 32. A voltage signal is generated across the electrodes 32, effectively at point C in FIG. 7, whose magnitude is dependent on whether the electrodes are in open circuit or whether they are in contact with the skin and are responsive to the skin impedance (represented as a resistor 48). This voltage signal is applied to a comparator 50, where it is compared with a threshold voltage output by the CPU 42. The comparator 50 generates a pulse output at point D of the circuit, in which the rising edge of each pulse corresponds with the voltage from the electrodes 32 increasing above the threshold level and the trailing edge of each pulse corresponds with the voltage from the electrodes 32 falling below the threshold level. A counter 52 within the CPU 42 also connected to the clock 44 counts the clock signal for the duration of each such pulse and thereby produces a numerical value representing the pulse duration. These numerical values are transmitted by way of a memory bus 54 to a memory or store 56.

The user control keys 38 can be employed for providing inputs to the CPU 42 to cause the CPU 42 to adjust the frequency, duration, and amplitude of the pulses supplied to the waveform generator 46 and to determine whether these pulses are supplied at regular intervals, or repeatedly in clusters. The waveform generator 46 is arranged to respond accordingly for supplying a corresponding AC waveform to the electrodes 32, and in this way the electrical impulses applied to the skin can be adjusted and treatment can be controlled. The CPU 42 processes the information obtained during a treatment session and displays the results on the display 36 as well as storing them in the memory 56. The CPU 42 is also arranged to activate one or more audio indicators 58 for signalling certain events in the treatment session.

In addition, a series connection of a switch 60 and a load 62 is connected across the two electrodes 32 and may be switched into the circuit in response to an output from the CPU 42, either in order to simulate skin contact when the electrodes 32 are not in contact with the skin of a patient or to provide a filter in cases of high skin sensitivity.

The signals at the various points of the circuit of FIG. 7 and in various circumstances are shown in FIGS. 8 to 13.

Figure 8:
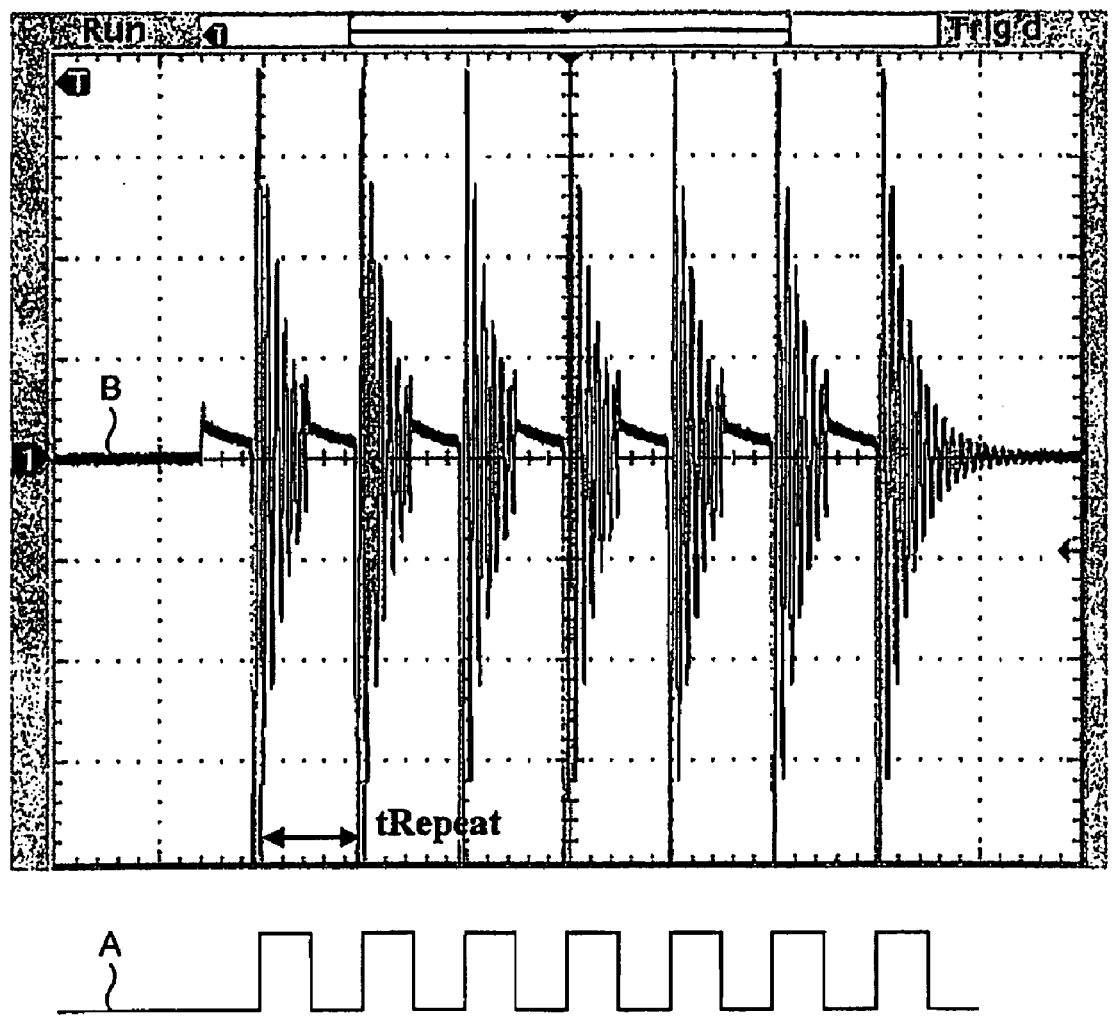
FIG. 8 is a waveform diagram showing an output of a waveform generator in the circuit of FIG. 7.
Figure 9:
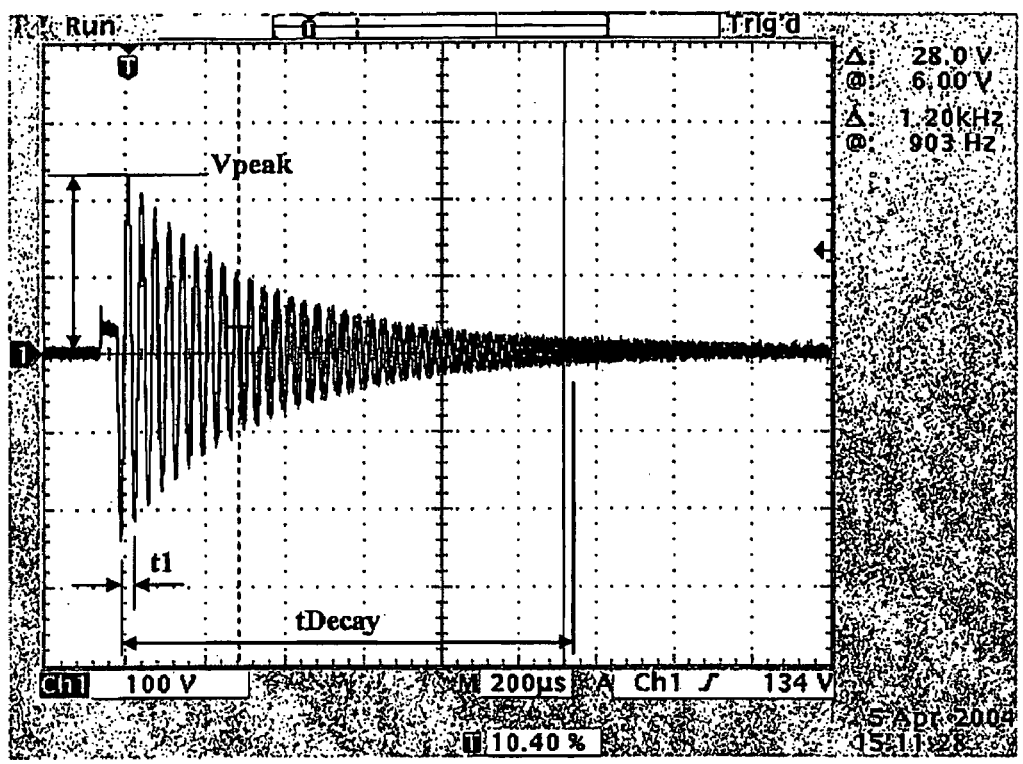
FIG. 9 is a waveform diagram showing a detail of the output of FIG. 8.
Figure 10:
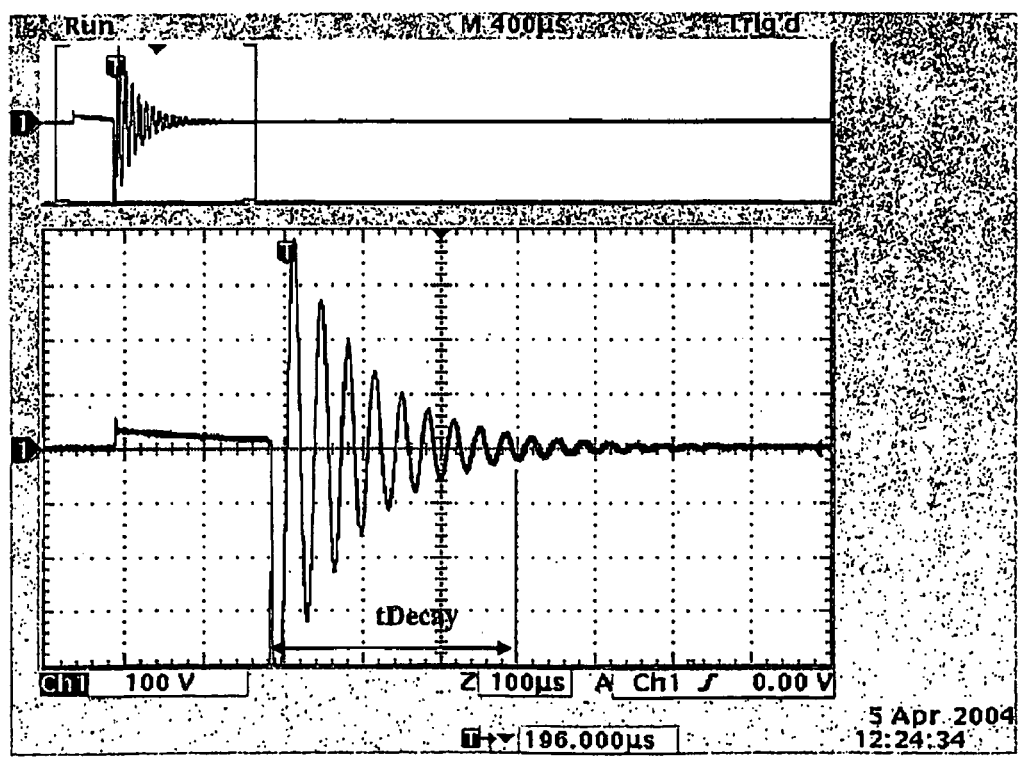
FIG. 10 is a waveform diagram showing the signal generated at one point of the circuit of FIG. 6 when the device is not in use but a load is connected across the electrodes to simulate skin contact.

FIG. 8 shows the rectangular pulse signal output by the CPU 42 and generated at the point A of the circuit, together with the corresponding repeated AC waveform output by the waveform generator 46 at point B of the circuit. A single cycle of the AC waveform at point B is shown in FIG. 9, and has an initial amplitude $V_{peak}$, a half wavelength $t_1$ and a decay $t_{decay}$. The amplitude $V_{peak}$ is dependent on the pulse width of the pulse signal at point A, which can be set by one of the control keys 38 according to a strength setting in a range from 1 to 250. In the example shown in FIG. 9, the strength setting is set to 20 and $V_{peak}$ is 230 volts. $t_1$ in this example is 40 microseconds and $t_{decay}$, to the point where the voltage has decayed to about 10% of $V_{peak}$, is 1.15 milliseconds.

The repetition rate of the AC waveform output by the waveform generator 46, as shown in FIG. 8, is determined by and corresponds with the frequency of the pulse signal at the point A and is set by the user from one of the control keys 38. The repetition rate is preferably adjustable from 50 Hz to 351 Hz. A further one of the control keys 38 sets whether the pulses output by the CPU 42 at the point A are generated at regular intervals or in clusters according to the intensity of the treatment required. The intensity of treatment can be set in a range from 1 to 8, representing the number of pulses, i.e. from 1 to 8, in each cluster. An intensity of 1 thus represents a series of pulses occurring at regular intervals, while an intensity of 8 represents clusters of 8 pulses at a time. The spacing between the individual pulses, or clusters of pulses, at the point A corresponds to the overall cycle time $t_{repeat}$ of each individual AC waveform, or cluster of waveforms, in the repeated cycle generated at the point B of the circuit and is also controlled by one of the user keys 38. This pulse spacing is defined as the gap in treatment applications, and the gap can be adjusted within the range from 10 to 80 corresponding to a spacing $t_{repeat}$ in a range from 220 microseconds to 1,600 microseconds.

By switching the load 62 into the circuit, the AC waveform output by the waveform generator 46 at the point B generates a waveform across the load 62 at the point E in FIG. 7. The waveform at the point E is a modification of the signal at the point B, in which the half wavelength $t_1$ is extended.

Figure 11:
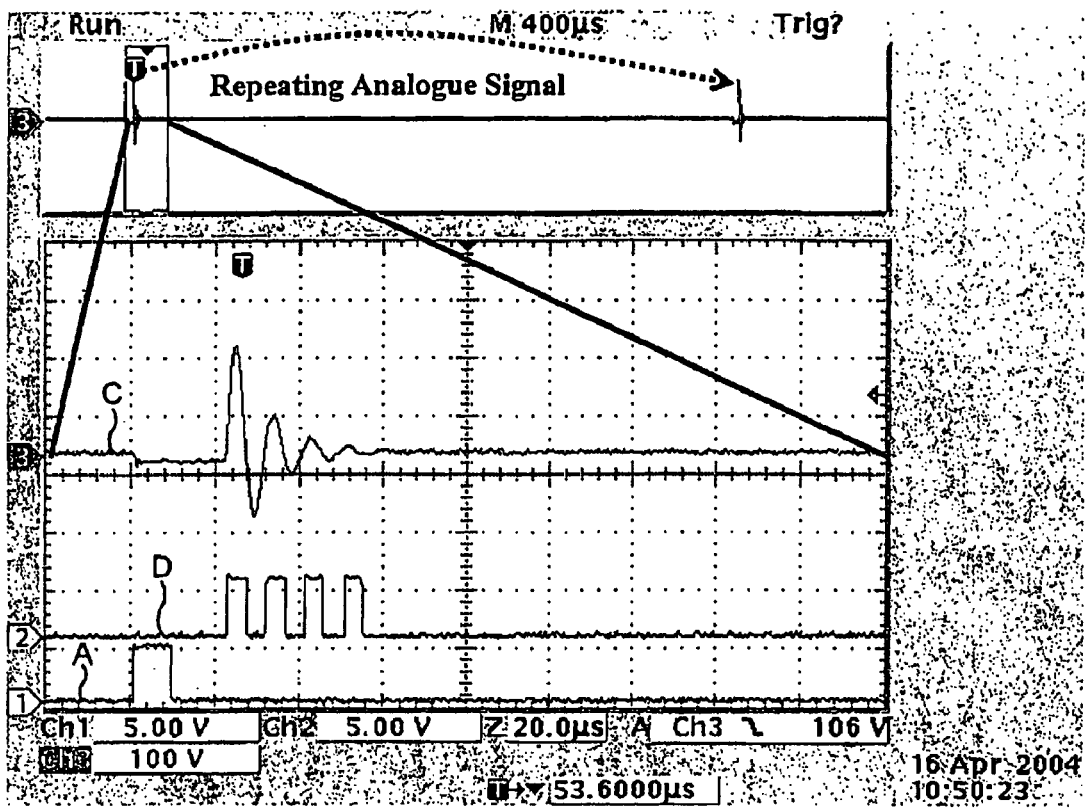
FIG. 11 is a signal diagram showing the signals generated at various points of the circuit of FIG. 7 when the treatment device is in use.

The signals described thus far effectively represent a situation where the treatment device 10 is not in contact with the skin and where the device remains unaffected by skin impedance. The signals arising in use of the device are shown in FIG. 11, which represents the events triggered by one pulse from the pulse signal at the point A and hence one full cycle of the AC waveform at the point B. As shown, the effect of the skin impedance results in a signal generated at the point C of FIG. 7, which is an AC waveform having an extended half wavelength $t_1$ and a fewer number of voltage peaks by comparison with the AC waveform at the point B. This signal at the point C is supplied to the comparator 50 where it is compared with a threshold voltage $V_{th}$. On each occasion that the signal at the point C increases above the threshold voltage the comparator 50 triggers the leading edge of a new pulse, and on each occasion that the signal at the point C falls below the threshold $V_{th}$ the comparator generates the trailing edge of a pulse. The pulse output of the comparator 50 at the point D of FIG. 7 is shown in FIG. 11.

Figure 12:
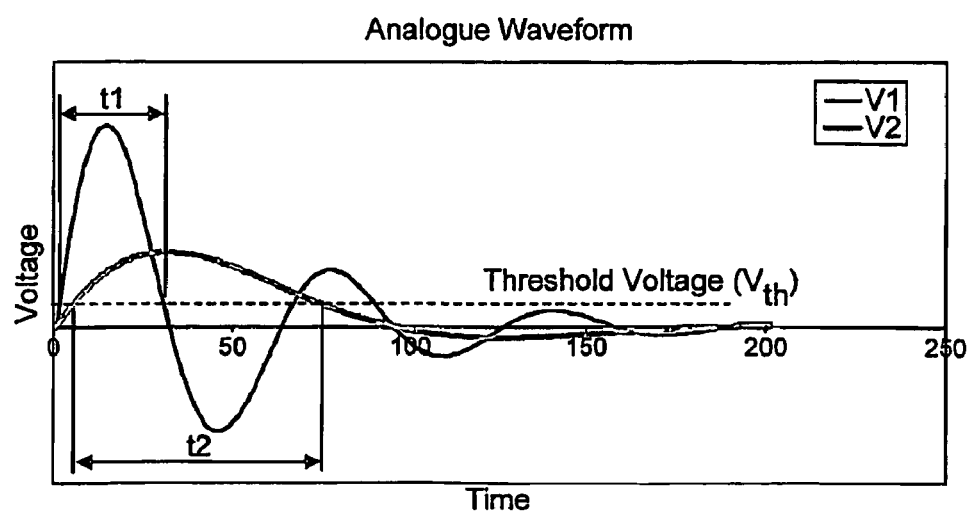
FIG. 12 is a waveform diagram showing how the signal at the electrodes of the treatment device varies in use as skin impedance changes.

It has been found that, as treatment continues, the skin impedance falls and consequently the signal at the point C becomes increasingly extended. This is illustrated in FIG. 12 where an initial response signal at the point C is represented by the line $V_1$ having a half wavelength $t_1$, and a subsequent response signal at the point C is represented by the line $V_2$ having a half wavelength $t_2$. It is evident that $t_1$ is less than $t_2$. Eventually, the response signal at the point C will have a half wavelength $t_0$, in which the threshold voltage is not exceeded at all.

Figure 13:
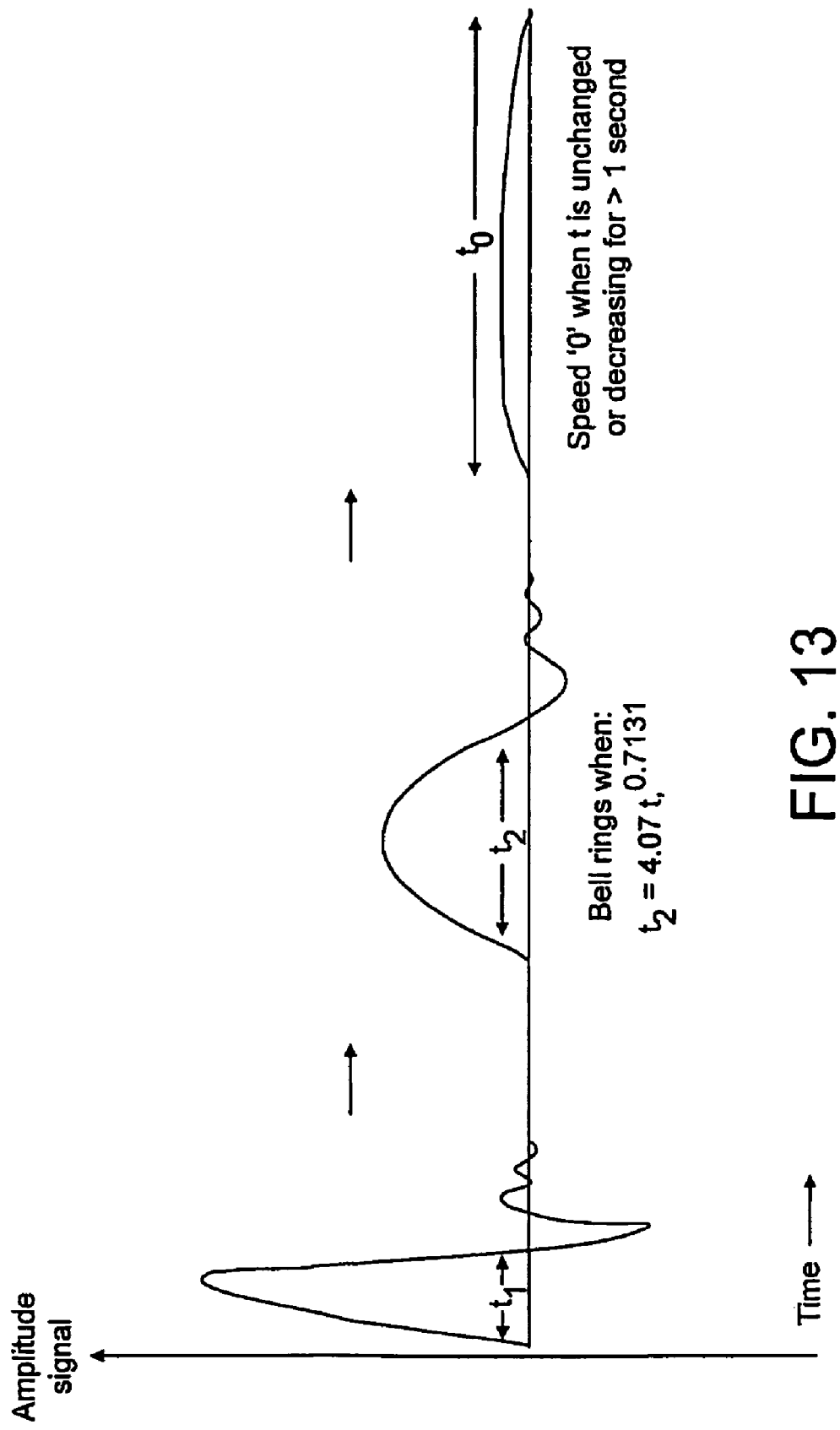
FIG. 13 is a waveform diagram corresponding to that of FIG. 12 and showing the waveform at the electrodes at three different time intervals.

This situation is represented in FIG. 13, which shows how the signal at the point C adapts as a treatment application progresses. Here, the initial skin impedance on first application of the AC waveform output by the waveform generator 46 at the point B is represented by the first signal in FIG. 13 and the half wavelength $t_1$; a subsequent application of the AC waveform at the point B is represented by the second signal in FIG. 13 and a half wavelength $t_2$; and a later application of the AC waveform at the point B is represented by the third signal and a half wavelength $t_0$.

Figure 14:
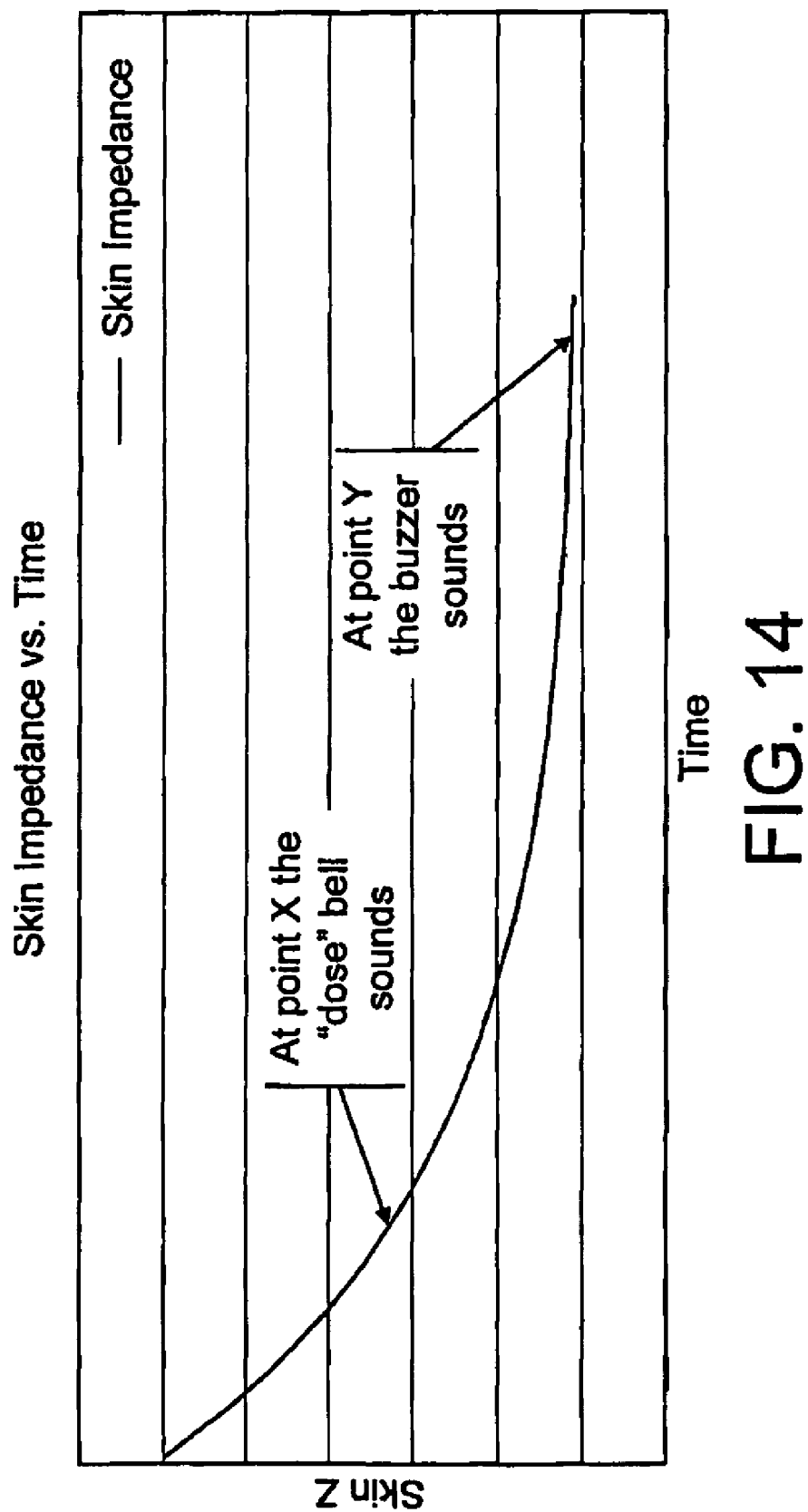
FIG. 14 is a graph representing the changes of skin impedance with time.
Figure 17:
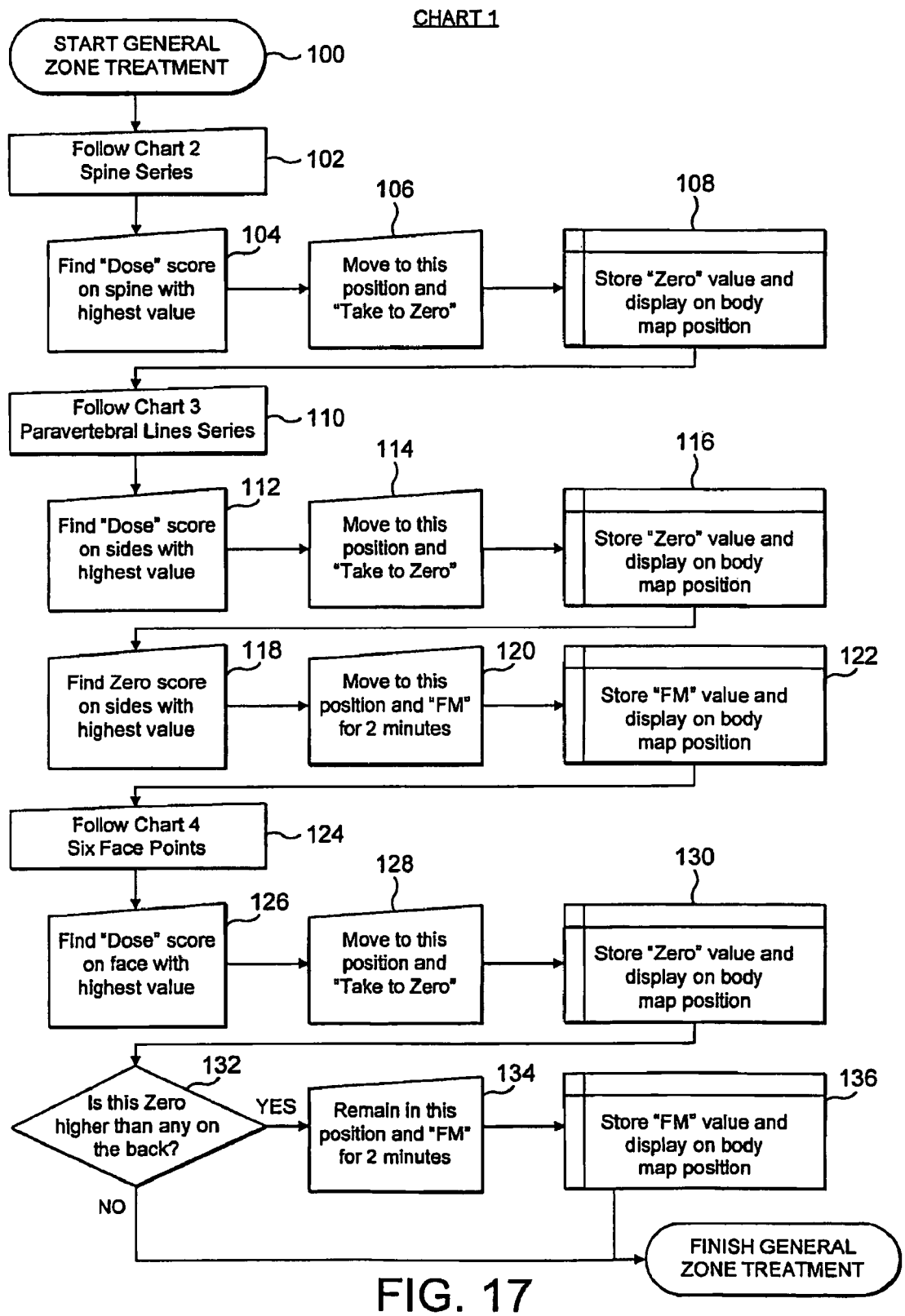
FIGS. 17 to 20 are flow charts representing software processing by a CPU of the treatment device shown in FIG. 7.

The graph in FIG. 14 represents the change of skin impedance with time for one specific zone only of a given area of the body. By monitoring this change, the CPU 42 can deduce how the patient is responding to the application of the electrical impulses. The time that it takes to reach the point X on the graph represents the responsivity of the skin of this particular body zone. Point X has been selected empirically to be the point, which satisfies the following equation:

$$t_2 = 4.087 \, t_1^{0.7131}$$

The point Y on the graph represents the point at which the rate of change of skin impedance Z with time t is zero, i.e.:

$$dZ/dt = 0$$

At the point Y, a standard treatment may be considered to have been administered. Referring back to FIG. 13, the second signal having the half wavelength $t_2$ corresponds to the point X in FIG. 14, and the third signal having the half wavelength $t_0$ corresponds to the point Y on the graph in FIG. 14.

In order to obtain a measurement corresponding to skin impedance, ideally the peak voltage values of each of the signals in FIG. 13 would be measured. However, it has been found more practical to measure the duration t of each initial half wave, and for this purpose the comparator 50 generates pulses in response to the crossings of the threshold voltage $V_{th}$ and the counter 52 counts to a numerical value determined in each instance by the generation of each pulse in the signal at the point D. These numerical count values are displayed on the display 36 of the device 10 under the control of the CPU 42.

Referring to FIG. 1, the initial reading for the count value corresponding to the half wavelength $t_1$ for the first signal in FIG. 13 occurring at the start of a treatment application is shown at the display location 36a at the top left hand corner of the display 36; the continually varying count value representing the half wavelength t as it changes during a treatment application is shown in the display location 36b in the lower left hand corner of the display 36, and a further count value representing the change of skin impedance with time, i.e. dZ/dt, and derived from counting the rate at which t changes is displayed at the display location 36c on the display 36. At the moment when the point X is reached on the graph in FIG. 14, the CPU 42 is arranged to trigger the audio indicator 58 to ring a bell. At the same time, the CPU 42 stops the counter 52 and the count value at the display location 36b is fixed and is stored in the memory 56. At the moment at which the point Y on the graph in FIG. 14 is reached, as represented by the value at the display location 36c showing zero, the CPU 42 is arranged firstly to trigger the audio indicator 58 to sound a buzzer and secondly to terminate generation of the pulse signal A.

The most basic operation of the handheld treatment device 10 will now be described.

Firstly, the physician switches the device on by means of the on/off switch 34 and sets the desired treatment strength and repetition rate by means of the control buttons 38. If desired, the physician also sets the desired treatment intensity and treatment gap by means of the control buttons 38, and decides whether or not to apply the filter provided by the load 62 and, if so, sets this with a further control key 38.

Next, the physician selects an area of the body for treatment and applies the electrical impulses to different body zones within this area. A number of initial readings will thus be generated and stored in the memory 56, and from the readings on the display location 36a the physician will select a number of zones with relatively high initial readings, representing a relatively high skin impedance, and will apply a treatment dose until the audio indicator 58 rings the bell. A new series of readings displayed at the display location 36b is thus generated and stored in the memory 56. The physician now selects the highest of this second series of readings and applies a further set of electrical impulses until the audio indicator 58 sounds the buzzer. At this moment, a final reading is obtained as shown at the display location 36b corresponding to a zero at the display location 36c, and this final reading is also stored in the memory 56.

In the preferred embodiment of the invention, the physician will in practice follow a precise treatment plan under the guidance of the CPU 42, and the display 36 will be arranged to alternate under the control of the CPU 42 between the display shown in FIG. 1 and one of the displays shown respectively in FIGS. 15 and 16. Such a treatment plan will now be described with reference to FIGS. 15 and 16 and the flow charts of FIGS. 17 to 20.

Referring firstly to FIGS. 15 and 16, these show two treatment maps 60 and 62 respectively. The map 60 represents the treatment of the back of a patient and the map 62 represents the treatment of a face of the patient. In the preferred embodiment, the display 36 of the treatment device 10 is arranged to alternate between the display shown in FIG. 1 and described above and a display showing one of the two maps 60 or 62. This alternation takes place either automatically under the control of the CPU 42 following the production of each new skin impedance reading. Alternatively, it is possible for the display to alternate between the two visual outputs on a timed basis or in response to user activation of a further control button 38. A further possibility is for the treatment device 10 to be connected to a PC during treatment, either by way of a physical connection line or by way of a wireless connection such as an infrared or bluetooth link, and to display the display of FIG. 1 on the device and the maps 60 and 62 on the screen of the PC.

In any event, each treatment map 60 and 62 comprises an outline 64 representing the predetermined area of the body being treated, the back in the case of FIG. 15 and the face in the case of FIG. 16. Within the outline 64 a series of map locations 66 are designated, each representing a different zone of the body area in question. The two maps shown in FIGS. 15 and 16 represent a completed treatment and therefore each map location contains one or more count values representing the skin impedance of the associated zone of the relevant body area. However, at the start of treatment, each map 60 and 62 will comprise simply the outline 64 and the series of designated positions.

The generation of the maps shown in FIGS. 15 and 16 during a treatment session will now be described with reference to the software steps shown in FIGS. 17 to 20.

It is assumed in the following description that treatment will start with the back of the patient. Treatment commences at step 100 in FIG. 17 with switching on the treatment device 10 by means of the on/off switch 34. Treatment of the back then commences with the sub routine represented in step 102 and shown in detail in FIG. 18, in which a series of readings are taken successively from the neck down the centre of the back following the line of the spine, represented by the line 68 in FIG. 15.

Figure 18:
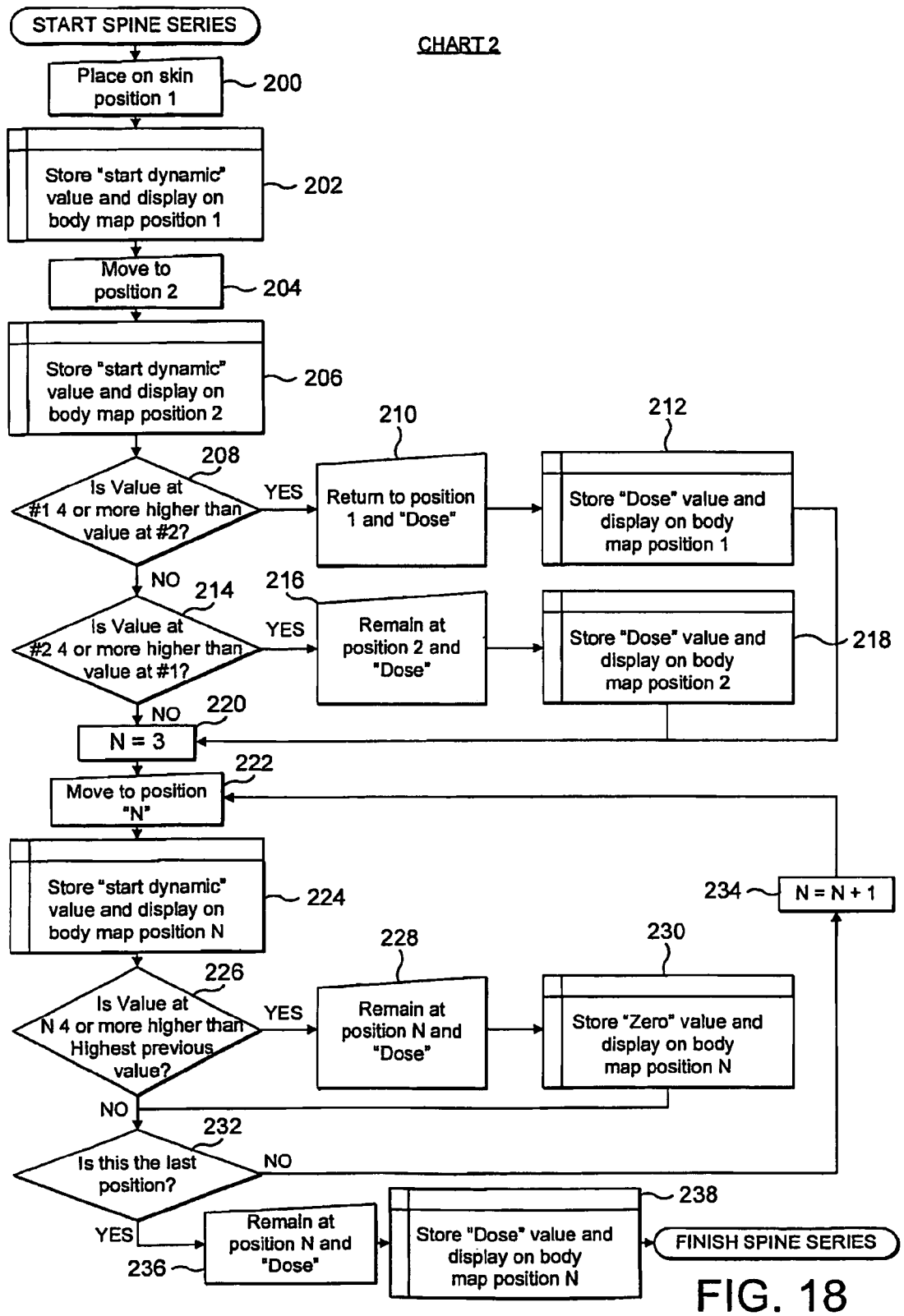

This sub routine 102 commences at step 200 in FIG. 18 when the treatment device 10 is placed on skin zone 1 at the top of the spine and a reading is taken. This reading yields the count value 24 from the counter 52 in the CPU 42 and is displayed as a start dynamic value at the display location 36a on the display 36 in FIG. 1. In step 202, the CPU stores the count value 24 in the memory 56 and switches the display 36 to the map 60 shown in FIG. 15 and displays the count value 24 at map location 1. The software then prompts the physician in step 204 to move the treatment device 10 to skin zone 2 and take a further reading. Such prompting may, for example, take the form of a light flashing on the display at the map location 2 corresponding to the skin zone 2. The physician takes a further reading and the display 36 reverts to its original display and displays this further initial reading or start dynamic value at the display location 36a in FIG. 1. Again, the new start dynamic value is stored in the memory 56 and the map 60 is brought up on the display with the count value 26 now shown in map location 2. This is represented in step 206.

In step 208, the software checks whether the count value at map location 1 is four or more higher than the count value at map location 2. If yes, the physician is prompted to move the treatment device 10 back to skin zone 1 and apply a treatment dose in step 210. A treatment dose is a series of electrical impulses applied until the position X is reached on the graph shown in FIG. 14 and until the audio indicator 58 rings the bell. The treatment dose given in step 210 will generate a corresponding count value in display location 36b on the display 36. The CPU 42 stores this dose count value in the memory 56 in step 212 and, reverting to the map 60, displays the dose value against map location 1. The dose value is indicated by a "star" on the map 60. On the other hand, if the answer to the question posed in step 208 is no, the software proceeds to step 214 and checks whether the value at map location 2 is four or more higher than the value at map location 1. If yes, the physician is prompted to maintain the treatment device 10 at skin zone 2 and to apply a treatment dose here in step 216. Once again, this generates a dose count value in the display location 36b in FIG. 1, and in step 218 the CPU 42 stores this dose count value in the memory 56 and, reverting to the treatment map 60, displays the dose count value in map location 2.

The software then proceeds from the relevant one of steps 212, 214 and 218 to step 220 in which the CPU 42 registers that the next skin zone to be treated is skin zone N, which is equivalent to skin zone 3. The device prompts the physician to move the treatment device 10 in step 222 to skin zone N, i.e. in this instance skin zone 3, and take a further reading. A new start dynamic count value is generated and in step 224 this is stored in the memory 56 and is displayed on the map 60 at map location N, which is at the third position in this instance. As shown in the specific example of FIG. 15, the start dynamic value at map location 3 is 32. In step 226, the software checks whether the start dynamic value at map location N (N=3) is four or more higher than the start dynamic values at the previous map locations. If yes, the physician is prompted to maintain the treatment device 10 at body zone 3 and to apply a treatment dose until the audio indicator 58 rings the bell. This is step 228. When the bell has rung and the dose count value is displayed at display location 36b on the display 36 in FIG. 1, the CPU stores the dose count value in the memory 56 and displays the value at map location N (N=3) in step 230.

Referring to FIG. 15, it will be seen that the specific example illustrated has a start dynamic count value of 32 in map location 3 and that this is the first occasion on which a value sufficiently high to prompt a treatment dose has been reached. The dose count value in this instance is shown to be 47.

In the case where the value at location N is not four or more higher than the previous highest start dynamic count value, the treatment process proceeds from step 226 directly to step 232 where the CPU 42 checks whether the final map location has been reached in the spine series. If no, the CPU 42 increments N by 1 in step 234 and returns to step 222. If yes, the CPU prompts the physician in step 236 to remain at skin zone N and apply a treatment dose. The dose count value is stored in step 238 in the memory 56 and is displayed on the treatment map 60. Referring to FIG. 15, the final location N is in fact shown above location 1 and represents the neck of the patient. The start dynamic count value here in this example is 28 and the dose count value is 45. This finishes the series of readings generated in the sub routine of step 102 and the CPU 42 returns to step 104 in FIG. 17.

In step 104, the software reviews the dose count values from the spine series and selects the one that has the highest value. The software prompts the physician in step 106 to move the treatment device to the relevant skin zone and to administer a full treatment. In this step, the physician holds the treatment device 10 at the relevant skin zone and applies electrical impulses until the point Y is reached in the graph in FIG. 14, i.e. until a value of zero representing dZ/dt is displayed at display location 36c of the display 36 in FIG. 1 and the audio indicator 58 sounds the buzzer. The reading at display location 36b at this moment is stored in step 108 in the memory 56 and is displayed on the map 60 at the relevant map location. In the example shown in FIG. 15, the full treatment is applied at body zone 5, represented by map location 5 on the map 60 and the full treatment value is shown as 120.

Figure 19:
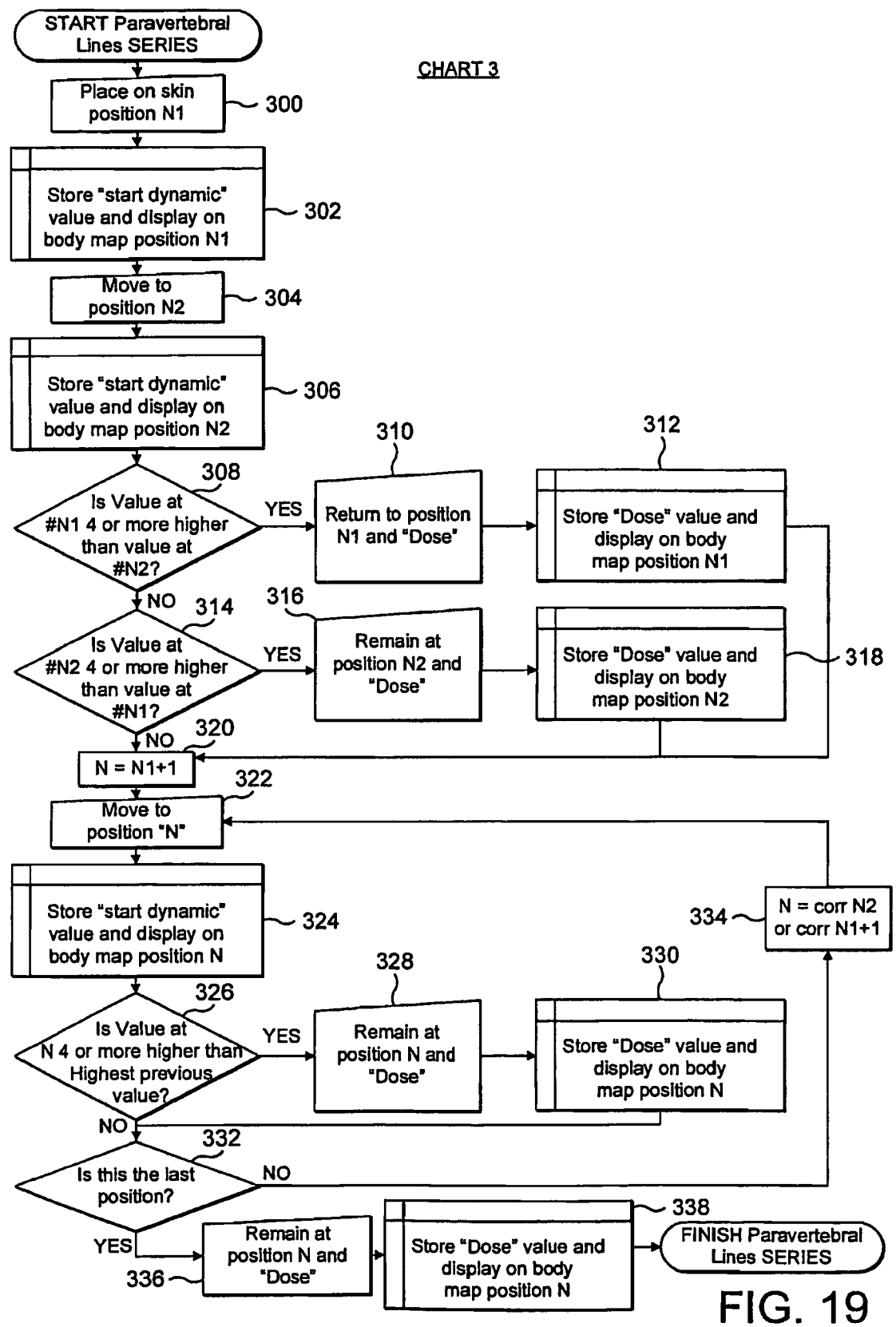

Having now completed a series of treatment applications along the spine of the patient, the treatment moves to the sub routine represented in step 110 and shown in FIG. 19 and readings are taken down the two paravertebral lines 70 and 72 flanking the spine.

The sub routine 110 commences at step 300, in which the device prompts the physician to place the treatment device 10 on skin zone N1=1, which is at the top of paravertebral line 70. The physician initiates the electrical impulses and a start dynamic count value for this skin zone is generated. In step 302, the software stores the new start dynamic count value in the memory 56 and displays the value at map location N1 corresponding to skin zone N1. In the example shown in FIG. 15, the start dynamic count value here is 31. In step 304, the software prompts the physician to move the treatment device 10 by one space down to position N1+1, and there another start dynamic count value is generated. This start dynamic count value is stored in the memory 56 and is then displayed at map location N1+1 of the map 60 in step 306. The software now considers in step 308 whether the start dynamic count value for body zone N1 is four or more higher than that for body zone N1+1. If yes, the software prompts the physician in step 310 to return to body zone N1 and apply a treatment dose. The dose count value thus generated is stored in the memory 56 and is displayed at map location N1 in step 312. If the answer to step 308 is no, however, the software proceeds to step 314 and enquires whether the start dynamic count value at body zone N1+1 is four or more higher than that at body zone N1. If yes, the software prompts the physician in step 316 to hold the treatment device 10 at body zone N1+1 and apply a treatment dose. The dose count value thus generated is stored in the memory 56 displayed at map location N1+1 in step 318.

Following step 312 or step 318, as appropriate, the software proceeds to step 320 where N1 is again incremented by 1 and prompts the physician in step 322 to move to the new body zone N1+2 and take a reading. The start dynamic count value thus generated is stored in the memory 56 and is displayed at map location N1+2 in step 324. In step 326, the software enquires whether the value and map location N1+2 is four or more higher than the highest previous start dynamic count value. If yes, the software prompts the physician in step 328 to remain at body zone N1+2 and apply a treatment dose. The dose count value thus generated is stored in the memory 56 and displayed at map location N1+2 in step 330. The software now proceeds to step 332. On the other hand, if the outcome of the enquiry in step 326 is no, the software proceeds immediately to step 332. Here the software enquires whether the last position of the lines 70 and 72 on the map 60 has been reached. If no, the software proceeds to step 334, increments N1 by another 1 and reverts to step 322. If yes, the software proceeds to step 336 and prompts the physician to remain at the final position and apply a treatment dose. The dose count value thus generated is stored in the memory 56 and displayed on the map 60 at the final position in step 338.

In the example shown in FIG. 15, the readings are first taken incrementally down the paravertebral line 70 finishing at the top of this line with a reading taken from the neck, and they then proceed down the paravertebral line 72 with the final position again being at the top of this line at the neck of the patient. This completes the sub routine of step 110.

The software now proceeds to step 112 in which it scans the dose count values from both paravertebral lines 70 and 72 and selects the one which is the highest. In step 114, the software prompts the physician to move the treatment device 10 to the corresponding skin zone and to apply a full treatment until the rate of change of skin impedance with time reaches zero. The treatment count value thus generated is stored in the memory 56 and displayed at the associated map location in step 116.

Referring to the example shown in FIG. 15, it will be seen that the highest dose count value for the two paravertebral lines 70 and 72 is at the fifth map location in line 70, being the value 65. At this map location, the further treatment value 98 obtained in step 116 is also displayed.

The software now proceeds to step 118 and scans the treatment count values in the whole of the map 60 and selects the one with the highest value. In step 120, the software prompts the physician to move the treatment device 10 to the associated body zone and to apply a further treatment, designated an FM treatment, for a period of two minutes. With reference to the example shown in FIG. 15, the highest treatment count value is at the fifth position of the spinal series of readings and is 120. The FM treatment in this instance is applied at the body zone corresponding to this map location.

During this frequency modulation treatment, the software in the CPU 42 generates a pulse output for supply to the waveform generator 46, which pulse output cycles through a range of frequencies from 15 Hz to 351 Hz with each successive cycle lasting for a duration of 8 seconds. The primary purpose of this further FM treatment is to access additional communication paths in the network 12 of nerves within the body in order to provide an additional healing stimulus. It is believed that the main treatment, which has been carried out up until this point, sets up a biofeedback loop along a dominant communication path. This generates the main healing stimulus. However, it is possible that there may also be other associated communication paths, which are either accessory to the main process or are linked to previous pathology. These other communication paths may not be addressed by the application of the main treatment through the biofeedback loop but may instead respond to electrical impulses applied at different frequencies. Thus, these other communication paths may be reached by cycling through the frequency range of the activation pulses, and it is for this reason that the final FM treatment is applied.

In step 122, the count value displayed at display location 36b on the display 36 in FIG. 1 at the culmination of the FM treatment is stored in the memory 56 and is displayed at the associated map location in step 122.

Figure 20:
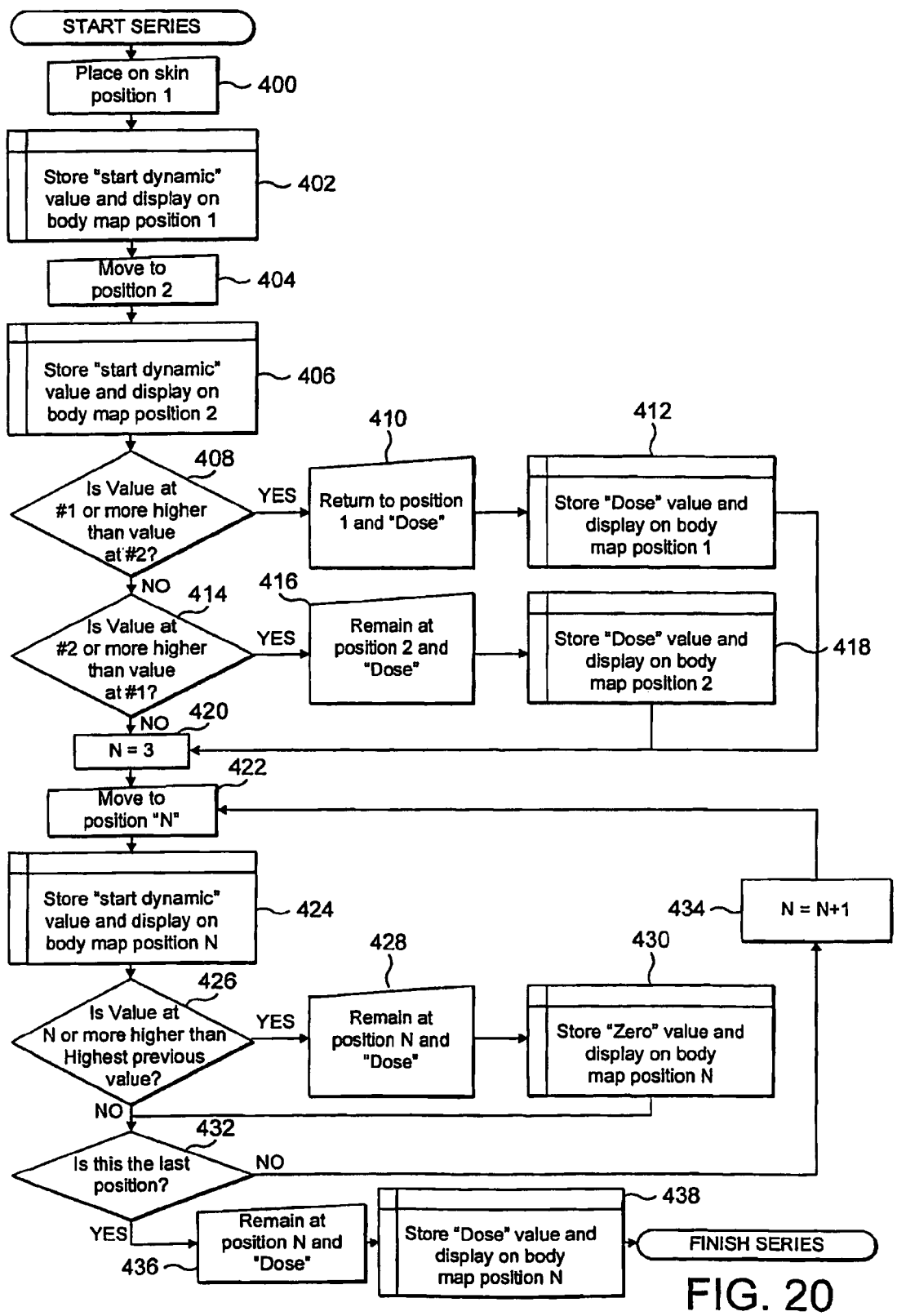

The software now proceeds to the sub routine represented in step 124 and shown in FIG. 20. This sub routine relates to the treatment of a patient's face and is represented by the map 62 shown in FIG. 16.

The sub routine 124 starts at step 400 in which the software sets the value N representing the relevant body zone on the patient's face to the value 1. In step 402, the software prompts the physician to move the treatment device 10 to the position N, i.e. initially the first position, and begin treatment. The start dynamic count value thus generated is stored in the memory 56 and is displayed at the corresponding map location on the facial map 62. In the example shown in FIG. 16, the first position is at the bottom left hand of the face and the corresponding start dynamic count value is 31.

The software proceeds to step 404 and prompts the physician to move the treatment device 10 to position 2, which is the lower right hand position of the face, and to begin treatment. The start dynamic count value for this body zone is stored in the memory 56 and is displayed on the facial map 62 at the map location 2, being the count value 36 in the example of FIG. 16. this is step 406. The software now proceeds to step 408 and enquires whether the count value for facial zone 1 is four or more higher than the count value for facial zone 2. If yes, the software prompts the physician to return to facial zone 1 and apply a treatment dose in step 410. The dose count value thus generated is stored in the memory 56 and displayed at map location 1 in step 412.

On the other hand, if the response to the enquiry of step 408 was no, the software proceeds to step 414 and enquires whether the start dynamic count value is four or more higher at facial zone 2 than at facial zone 1. If yes, the software prompts the physician in step 416 to remain at facial zone 2 and apply a treatment dose. The dose count value thus generated in stored in the memory 56 and displayed at map location 2 in step 418. In the example shown in FIG. 16, the start dynamic count value at map location 2 is 36 which fulfils the enquiry at step 414, and a corresponding dose count value of 51 is displayed. The software then proceeds from step 418 to step 420. If the enquiry at step 414 yields the answer no, the software also proceeds to step 420 in which the value N is incremented by 1.

Next in step 422, the software prompts the physician to move the treatment device 10 to facial zone 3, which is at the centre left of the face, and to begin treatment. A new start dynamic count value is generated and in step 424 this is stored in the memory 56 and is displayed at the corresponding map location of the facial map 62. In step 426, the software enquires whether the start dynamic count value at the third map location, which represents the third facial zone, is four or more higher than the highest previous start dynamic count value for the face. If yes, the software proceeds to step 428 and prompts the physician to apply a treatment dose at this zone. In step 430, the dose count value thus generated is stored in the memory 56 and is displayed on the facial map 62 at the third map location. The software now proceeds to step 432. On the other hand, if the response to the enquiry at step 426 is no, the software proceeds directly to step 432 and enquires whether the last facial zone has been reached. If no, the software increments the value N by 1 in step 434 and reverts to step 422. If yes, the software proceeds to step 436 and applies a treatment dose at the last facial zone. The dose count value thus generated is stored in the memory 56 and displayed at the corresponding map location in step 438.

With reference to FIG. 16, the last facial zone is the one at the top right hand side of the face where, in the example given, the start dynamic count value is displayed as 38 and the dose count value is displayed as 53. This completes the sub routine of step 124 and the software now proceeds to step 126. Here, the software scans the dose count values for the facial zones stored in the memory 56 and selects the one with the highest value. The software then prompts the physician in step 128 to move the treatment device 10 to the corresponding facial zone and apply a full treatment. The count value generated at the moment when dZ/dt becomes zero is stored in the memory 56 and is displayed on the facial map 62 in step 130. Referring to the facial map 62 in FIG. 16, the highest dose count value is seen to be at the top left hand side of the face, being 58, and the full treatment is applied at the corresponding facial zone and yields a full treatment count value 87.

The software now proceeds to step 132 and scanning the values in the memory 56 enquires whether the full treatment count value for the face is higher than the full treatment count values for the back. If no, the treatment is finished. If yes, the software proceeds to step 134 and prompts the physician to remain at this facial zone and apply an FM treatment for a duration of two minutes. This FM treatment yields a further count value, which in step 136 is stored in the memory 56 and displayed at the corresponding map location.

The treatment is now finished.

The above description of a treatment session with the aid of the treatment maps 60 and 62 shown respectively in FIGS. 15 and 16 and the flowcharts shown in FIGS. 17 to 20 assumes that the software in the CPU 42 is designed to undertake all the processing to evaluate which body zones should receive treatment doses and which body zones should receive full treatment and is designed also to prompt the physician to move in each case to the relevant body zone. It is, of course, also possible to employ a simplified form of the software, in which the software simply reads the treatment values and stores the relevant readings in the memory 56 and displays them on the treatment maps. In this case, the physician firstly selects each new position for the treatment device 10 by inspection of the treatment map, and secondly selects the relevant body zones for receiving treatment doses and full treatment by inspection of the treatment map.

In a further application of the present invention, the treatment device 10 may be employed as part of a treatment system in which the results of each treatment session may be transferred from the treatment device 10 to a practitioner's PC and thence to a server database for holding full details of a patient's history. Easy access to the server database may be controlled by means of a smart card for accessing the patient's details for each new treatment session, whether they are visiting their original practitioner or a different one. This treatment system is shown in FIGS. 21 to 24.

Figure 21:
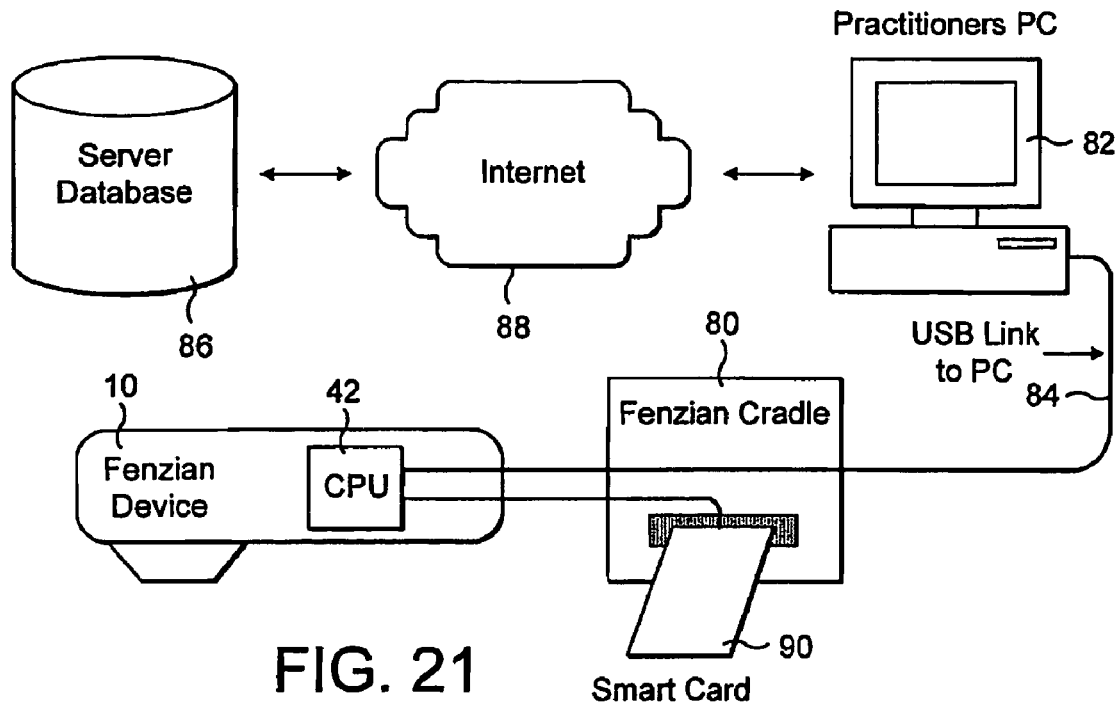
FIG. 21 is a block diagram of a treatment system incorporating the treatment device of FIGS. 1 to 20.

Referring to FIG. 21, the treatment system comprises the treatment device 10 with its CPU 42, and a cradle 80 for receiving the treatment device 10. The cradle 80 is connected to a practitioner's PC 82, for example by way of a USB link 84, for communicating information between the treatment device 10 and the PC 82. The cradle 80 may also contain a charger (not shown) for charging the battery 40 in the treatment device 10. The practitioner's PC 82 has access to a server database 86 by way of the Internet 88 or other communication mode. By these means, the results of each treatment session stored in the memory 56 of the treatment device 10 may be downloaded to the practitioner's PC 82 and thence to the server database 86. Correspondingly, the results of any previous treatment sessions may be accessed by the practitioner through the PC 82, and relevant information may be downloaded to the treatment device 10 for reference in a new treatment session.

In order to control access to such information, and hence to ensure that confidentiality is maintained and that a patient's record can only be accessed in association with the patient, the patient may carry a smart card 90 bearing a security PIN. The cradle 80 is designed to receive the smart card 90, and the CPU 42 in the treatment device 10 is designed to be able to read the smart card 90 for accessing the relevant records on the server database 86 by way of the PC 82. The events, which take place during the first and subsequent treatment sessions in this respect, are shown in FIGS. 22 and 23, and the software in the CPU 42 and corresponding steps are shown in FIG. 24.

Figure 22:
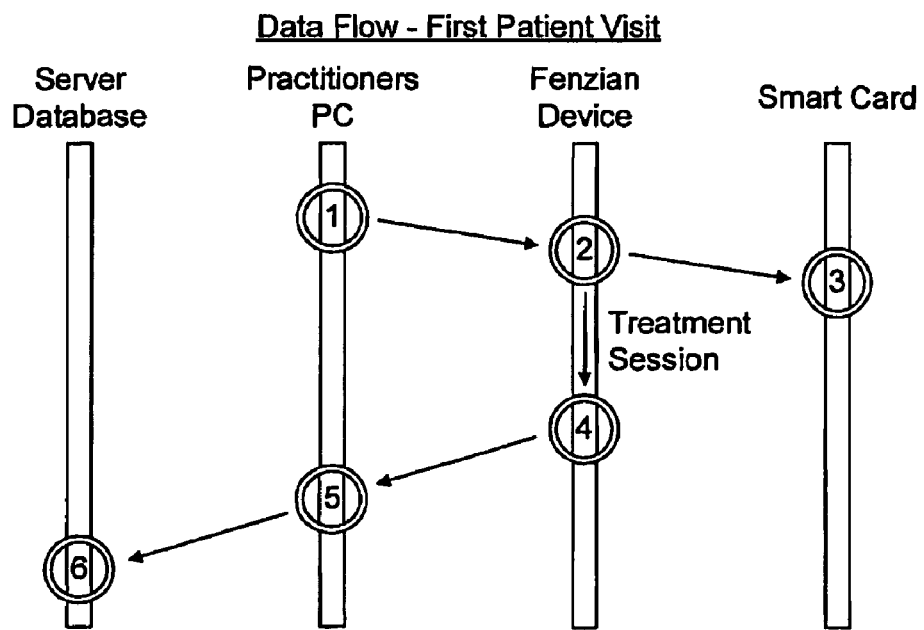
FIGS. 22 and 23 are data flow diagrams representing use of the treatment system of FIG. 21.

Referring initially to FIG. 22, in the first treatment session, the patient fills in a registration form for the practitioner. The practitioner enters the data from the registration form into the PC 82 as the patient record as event 1 in FIG. 22. The treatment device 10 accesses the patient record as event 2 and using the information in the patient record applies a unique patient ID to a blank card 90 inserted in the cradle 80 to create a new smart card. This is event 3 in FIG. 22. Subsequently, the practitioner administers a treatment session, the results of which are recorded in the memory 56 of the CPU 42 as previously described. After the treatment session, as event 4 in FIG. 22, the treatment device 10 is returned to the cradle 80, and then the results of the treatment session are transferred from the treatment device 10 to the PC 82 as event 5. Subsequently, both the patient record on the PC 82 and the results of the treatment session are transferred from PC 82 to the server database 86 as event 6. The patient takes the smart card 90 and departs.

Figure 23:
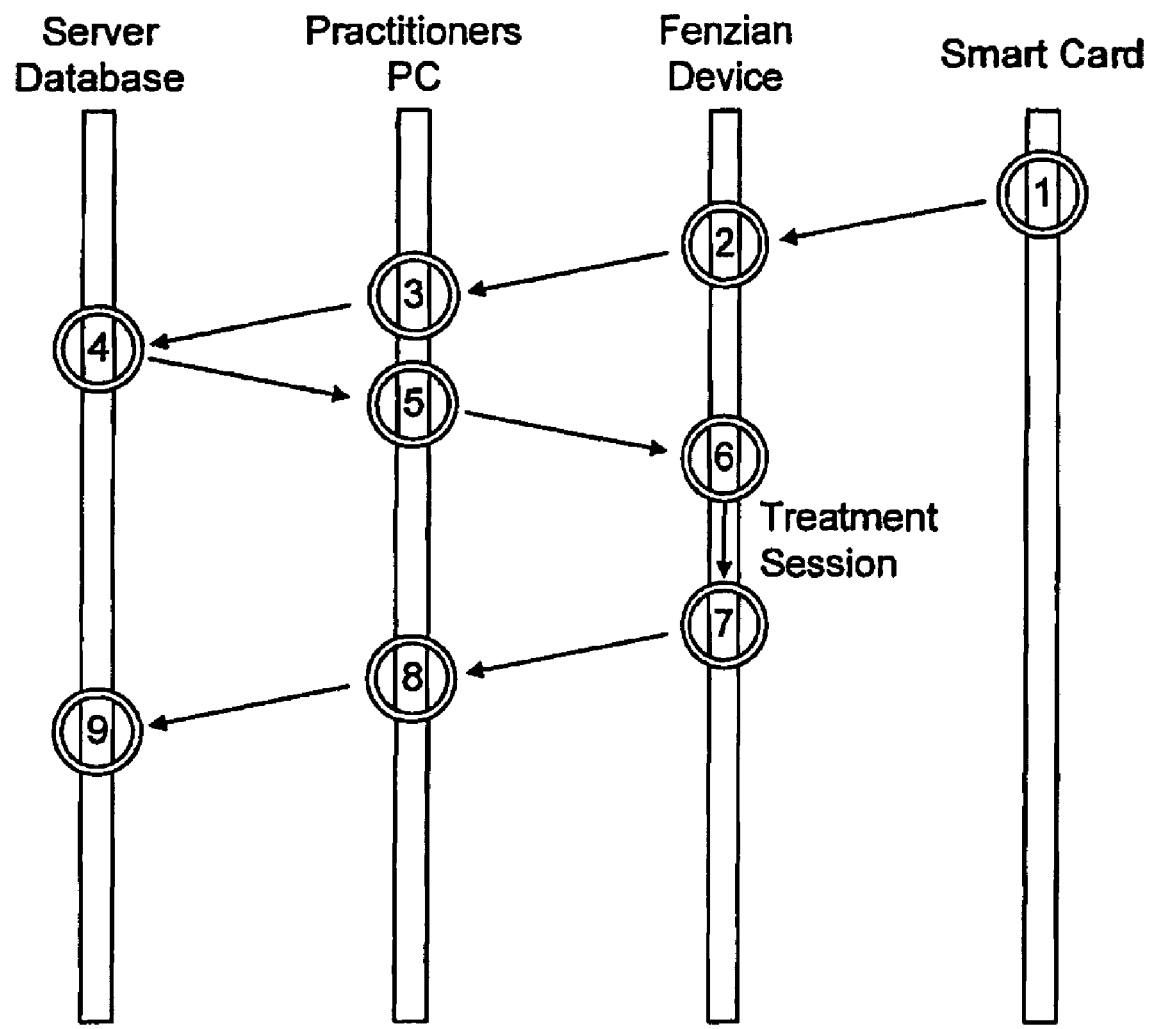

In a subsequent treatment session, represented in FIG. 23, the session commences with the patient inserting the imprinted smart card 90 into the cradle 80 as event 1. The CPU 42 of the treatment device 10 reads the unique patient ID from the smart card 90 as event 2 in FIG. 23, and transfers the patient ID to the PC 82 as event 3. As event 4, the PC 82 supplies the patient ID to the server database 86 and then during event 5 retrieves the patient records from the server database 86. The treatment device 10 then retrieves any relevant information from the PC 82 as event 6 for use during the treatment session. The treatment device 10 records the results of the treatment session, following which the practitioner replaces the treatment device 10 in the cradle 80 as event 7. The results of the treatment session are now transferred as event 8 from the treatment device 10 to the PC 82. Finally, as event 9, the full patient record with the results of the treatment session are transferred from the PC 82 to the server database 86, and the patient retrieves the smart card 90 from the cradle 80.

Figure 24:
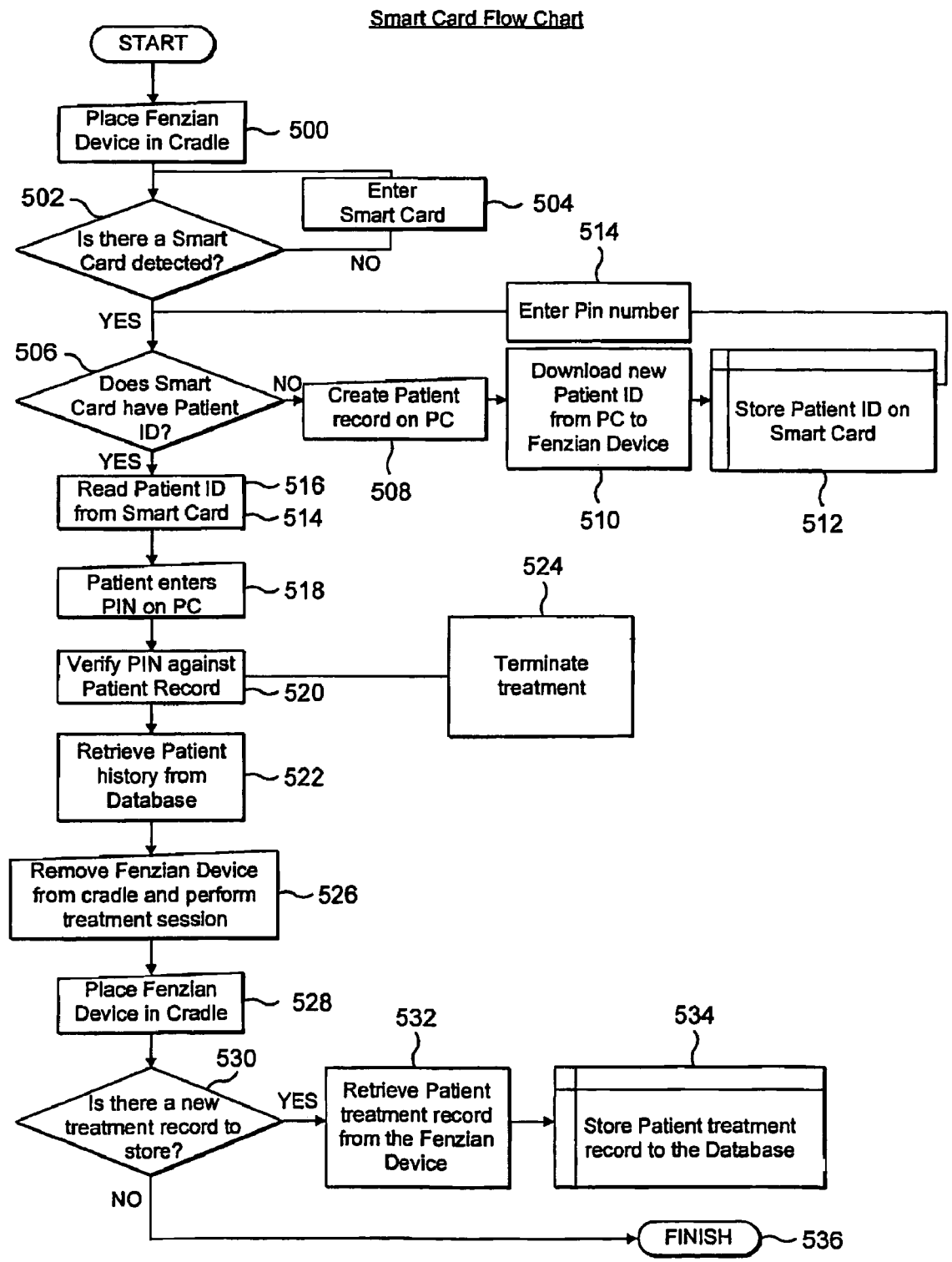
FIG. 24 is a flowchart representing software processing by the CPU of the treatment device in the application of the device in the treatment system of FIG. 21.

The processing steps, which take place within the CPU 42 of the treatment device 10 during these events, are shown in FIG. 24 and will now be described.

At the start of a treatment session, whether this is the first or a subsequent treatment session, the practitioner places the treatment device 10 in the cradle 80 in step 500. The software of the CPU 42 interrogates the cradle 80 to discover whether a smart card is detected. This is step 502. If no, the software proceeds to step 504 and prompts the practitioner to request the patient to enter a smart card. The software then reverts to step 502. On the other hand, if a smart card is detected, the software proceeds to step 506 and interrogates the smart card 90 to establish whether it carries a unique patient ID. If no, the software proceeds to step 508 and prompts the PC 82 to create a new or select an existing patient record. The treatment device 10 then requests the PC 82 to download the patient ID to the treatment device 10 by way of the cradle 80 in step 510. The software reads the patient ID and stores this ID on the smart card 90 in step 512 and then proceeds to step 514 and requests the patient to enter a new PIN number by way of a keypad (not shown) on the cradle 80.

The software then reverts to step 506 and enquires whether a smart card 90 is detected in the cradle 80. If yes, the software proceeds to step 516 and the treatment device 10 reads the patient ID from the smart card, and then prompts the patient in step 518 to enter their PIN number via the keypad on the cradle 80. The software verifies the PIN number that has been input against the unique patient ID on the smart card in step 520. If the two match, the treatment device 10 requests the patient history from the PC 82 in step 522. The PC 82 retrieves the patient history from the server database 86 and supplies the relevant information to the treatment device 10. On the other hand, if the PIN number and the patient ID do not match, the software terminates the treatment in step 524.

Once the treatment device 10 has the necessary information, the practitioner removes the device from the cradle 80 and performs a treatment session, during which the treatment results are stored in the memory 56 of the device in step 526. After the treatment session, the practitioner replaces the treatment device 10 in the cradle 80, at which point in step 528 the software detects the presence of the cradle 80 and proceeds to step 530. In step 530, the treatment device 10 enquires whether the PC 82 is ready to receive a new treatment record. If yes, the treatment device 10 downloads the results of the treatment session to the PC 82 by way of the cradle 80 in step 532. Then, in step 534 the treatment device 10 requests the PC to transmit the treatment record to the server database 86. On the other hand, if the results of the enquiry of step 530 are no, for any reason, the treatment device 10 retains the treatment results in its memory 56 and terminates the treatment session in step 536.

In the described embodiment, most of the processing is conducted within the CPU 42 of the handheld device 10. However, it will be appreciated that various modifications are possible within the scope of the invention. For example, some of the processing can be shared with the CPU in the practitioner's PC 82 as also can some of the display features.

Other modifications are also possible. For example, the comparator 50 for detecting feedback signals from the electrodes 32 may be replaced by alternative detection means. Instead of measuring the duration of the pulses output by the comparator for detecting the time between crossings of the feedback waveform, detection means for measuring the peak value of the feedback waveform or the area between the feedback waveform and a threshold line may be employed.

Other possible variants include the replacement of the audio indicator 58 with a visual indicator and the replacement of the control buttons 38 with different control input means.

The treatment device and method of the present invention have numerous significant advantages.

In particular, it has been found that the treatment device of the present invention as described above is capable of effectively treating a wide variety of illness and disease, as well as other clinical conditions. The device also has the advantages of being portable and easy to use and relatively inexpensive to manufacture and produce.

Further the provision of patient records for future referral is of significant benefit in monitoring the progress and outcome of treatment.

The invention claimed is:

1. Treatment apparatus for applying electrical impulses to a living body through the skin, for non-invasively treating a variety of clinical conditions, comprising:
   a pair of co-located electrodes for surface contact with the skin;
   a waveform generator for repeatedly generating an AC waveform for applying electrical impulses through the electrodes to the skin;
   means responsive to a resistance generated between the electrodes due to skin impedance for detecting the responsivity of respective zones of a pre-determined area of the body and for producing output data representing the responsivity of each said respective zone;
   means for converting the output data into measurement values;
   a processor for generating a treatment map of the said pre-determined area of the body having at respective map locations corresponding to said respective zones the associated measurement values;

a display for displaying said treatment map including said measurement values at said respective map locations;

a store for storing information relating to the treatment map; and means for selecting a treatment zone from amongst the said respective zones based on an evaluation of the measurement values displayed at the map locations on the treatment map, in order to select the respective zone of greatest responsivity; and wherein the waveform generator is thereafter operable for generating the said AC waveform for administering a treatment through the co-located electrodes at the said selected treatment zone.

2. Treatment apparatus according to claim 1, in which the selecting means evaluates the data according to the highest measurement value.

3. Treatment apparatus according to claim 1, in which the processor provides the selecting means with the measurement values the selecting means selects the said zone of greatest responsivity based on a comparison of the measurement values.

4. Treatment apparatus according to claim 1, in which the treatment map displayed on the display comprises a body map having an outline representing the predetermined area of the body, and wherein said map locations are located within the outline at positions corresponding to the respective zones of the predetermined area of the body.

5. Treatment apparatus according to claim 1, in which following the detection of the responsivity of each respective zone the processor is arranged to present the associated measurement value at the corresponding map location on the display.

6. Treatment apparatus according to claim 1, wherein the processor is further capable of guiding the means for selecting the treatment zone according to a treatment plan.

7. Treatment apparatus according to claim 1, wherein the processor is further capable of guiding the means for detecting responsivity for collecting output data according to a treatment plan.

8. Treatment apparatus according to claim 6, in which the processor is arranged to generate prompts on the display to indicate the selected treatment zone.

9. Treatment apparatus according to claim 7, in which the processor is arranged to generate prompts on the display to guide the means for detecting responsivity.

* * * * *